(12) United States Patent
Li et al.

(10) Patent No.: US 11,850,291 B2
(45) Date of Patent: Dec. 26, 2023

(54) PSMA TARGETED RADIOTHERAPY MEDICINE AND PREPARATION METHOD THEREOF

(71) Applicants: Ming-Hsin Li, Taoyuan (TW);
Sheng-Nan Lo, Taoyuan (TW);
Shih-Wei Lo, Taoyuan (TW);
Shih-Ying Lee, Taoyuan (TW);
Su-Jung Chen, Taoyuan (TW);
Shih-Min Wang, Taoyuan (TW);
Ming-Wei Chen, Taoyuan (TW);
Wei-Lin Lo, Taoyuan (TW)

(72) Inventors: Ming-Hsin Li, Taoyuan (TW);
Sheng-Nan Lo, Taoyuan (TW);
Shih-Wei Lo, Taoyuan (TW);
Shih-Ying Lee, Taoyuan (TW);
Su-Jung Chen, Taoyuan (TW);
Shih-Min Wang, Taoyuan (TW);
Ming-Wei Chen, Taoyuan (TW);
Wei-Lin Lo, Taoyuan (TW)

(73) Assignee: NATIONAL ATOMIC RESEARCH INSTITUTE, Taoyuan (TW)

( * ) Notice: Subject to any disclaimer, the term of this patent is extended or adjusted under 35 U.S.C. 154(b) by 464 days.

(21) Appl. No.: 16/663,387

(22) Filed: Oct. 25, 2019

(65) Prior Publication Data
US 2021/0121585 A1  Apr. 29, 2021

(51) Int. Cl.
*A61K 51/08* (2006.01)

(52) U.S. Cl.
CPC ................................. *A61K 51/088* (2013.01)

(58) Field of Classification Search
CPC ...... A61K 51/00; A61K 51/08; A61K 51/088; A61K 51/04; A61K 51/0497; A61K 51/0402
USPC .... 424/1.11, 1.65, 1.69, 9.1, 9.2; 514/1, 1.1, 514/19.2, 19.3, 19.4, 19.5, 19.6; 534/7, 534/10–16
See application file for complete search history.

(56) References Cited

PUBLICATIONS

Lutje et al, Theranostics, vol. 5, Issue 12, pp. 1388-1401 (Year: 2015).*

* cited by examiner

*Primary Examiner* — D. L. Jones

(57) ABSTRACT

The invention features a novel precursor provided for radio-isotope labeling with ligands for specific binding of prostate-specific membrane antigen (PSMA) for prostate cancer diagnosis and treatment, and the pharmacophore of a PSMA inhibitor composed of three molecules of glutamic acid, urea and lysine is provided with three variable linkers based on pharmacological activity of the PSMA inhibitor for labeling with radioactive nucleus Ga-67, Ga-68, In-111, Lu-177, Cu-64, or Y-90 through a chelating agent for imaging analysis of human tumor models of prostate cancer and serving as a PSMA-targeted radioligand therapy for prostate cancer diseases.

3 Claims, 37 Drawing Sheets

| | Radiolabeling condition | | | | | |
|---|---|---|---|---|---|---|
| No. | MH-PC-NAB-1 | $^{68}GaCl_3$ (Initial activity) | $^{68}GaCl_3$ (Specific activity) | 3M NaOAc (pH7-8) | Temp. and incubation time | Final Reaction Volume |
| 1 | 20μg (2μL) | 1.64mCi/500μL | 4.82μCi/μL | 18μL (pH 3.7) | 95 °C, 10 mins | 520μL |
| 2 | 20μg (2μL) | 1.66mCi/500μL | 4.44μCi/μL | 30μL (pH 4.7) | 95 °C, 10 mins | 532μL |
| 3 | 20μg (2μL) | 2.82mCi/500μL | 5.64μCi/μL | 30μL (pH 4.7) | 95 °C, 10 mins | 532μL |
| 4 | 20μg (2μL) | 2.04mCi/500μL | 4.08μCi/μL | 30μL (pH 4.7) | 95 °C, 10 mins | 532μL |

| | Quality control | | | |
|---|---|---|---|---|
| No. | Crude Product | pH | Radiochemical purity | |
| | | | Radio-TLC | Radio-HPLC |
| 1 | 1.41 mCi/520μL | 3.5-4.0 | 100% | 100% |
| 2 | 1.42 mCi/532μL | 4.5-5.0 | 100% | 97.3% |
| 3 | 2.49 mCi/532μL | 4.5-5.0 | 100% | 100% |
| 4 | 1.81mCi/532μL | 4.5-5.0 | 100% | 100% |

FIG. 15

| Radiolabeling condition | | | | | |
|---|---|---|---|---|---|
| No. | MH-PC-AB-9 | $^{111}InCl_3$ (Initial activity) | $^{111}InCl_3$ (Specific activity) | 1.0 M NaOAc (pH6.0) | Temp. and incubation time | Final Reaction Volume |
| 1 | 20μg (1μL) | 3.04mCi/ 150μL | 20μCi/μL | 99 μL | 95 °C, 15 mins | 150μL |

| Quality control | | |
|---|---|---|
| No. | Crude Product | Radiochemical purity |
| | | Radio-TLC |
| 1 | 3.08 mCi/152μL | 96.7% |

FIG. 19

| | Radiolabeling condition | | | | |
|---|---|---|---|---|---|
| No. | MH-PC-AB-52 | $^{111}InCl_3$ (Initial activity) | $^{111}InCl_3$ (Specific activity) | 1.0 M NaOAc (pH6.0) | Temp. and incubation time | Final Reaction Volume |
| 1 | 20μg (1μL) | 3.04mCi/37μL | 20μCi/μL | 114μL | 95 °C, 15 mins | 152μL |

| | Quality control | |
|---|---|---|
| | | Radiochemical purity |
| No. | Crude Product | Radio-TLC |
| 1 | 3.08 mCi/152μL | 95.9% |

FIG. 22

| Radiolabeling condition | | | | |
|---|---|---|---|---|
| No. | MH-PC-AB-52 | $^{111}InCl_3$ (Initial activity) | $^{111}InCl_3$ (Specific activity) | 1.0 M NaOAc (pH6.0) | Temp. and incubation time | Final Reaction Volume |
| 1 | 20µg (1µL) | 3.13mCi/9µL | 354 µCi/µL | 290µL | 95 °C, 15 mins | 300µL |

| Quality control | | |
|---|---|---|
| No. | Crude Product | Radiochemical purity Radio-TLC |
| 1 | 3.16mCi/300µL | 96.8% |

FIG. 25

| ROI ratio | 0.5h | | | 2h | | | 4h | | |
|---|---|---|---|---|---|---|---|---|---|
| MH-PC-AB-X | T/M ratio | T/L ratio | T/K ratio | T/M ratio | T/L ratio | T/K ratio | T/M ratio | T/L ratio | T/K ratio |
| 68Ga-MH-PC-NAB-1 (n=3) | 11.5 | 5.8 | 0.4 | 77.3 | 17.1 | 0.9 | 105.5 | 20.4 | 0.8 |

| MH-PC-AB-X | Tumor (%ID/g) | | | Kidney (%ID/g) | | | Liver (%ID/g) | | |
|---|---|---|---|---|---|---|---|---|---|
| | 0.5h | 2h | 4h | 0.5h | 2h | 4h | 0.5h | 2h | 4h |
| 68Ga-MH-PC-NAB-1 (n=3) | 7.3±7.6 | 10.2±7.1 | 7.9±7.8 | 15.1±4.1 | 11.0±2.6 | 8.3±2.4 | 1.1±0.5 | 0.6±0.2 | 0.4±0.0 |

FIG. 29

| ROI ratio / MH-PC-AB-X | 1h T/M ratio | 1h T/L ratio | 1h T/K ratio | 4h T/M ratio | 4h T/L ratio | 4h T/K ratio | 24h T/M ratio | 24h T/L ratio | 24h T/K ratio | 48h T/M ratio | 48h T/L ratio | 48h T/K ratio | 72h T/M ratio | 72h T/L ratio | 72h T/K ratio | 96h T/M ratio | 96h T/L ratio | 96h T/K ratio |
|---|---|---|---|---|---|---|---|---|---|---|---|---|---|---|---|---|---|---|
| 111In-MH-PC-AB-9 (n=3) | 2.4 | 2.7 | 0.4 | 4.7 | 4.2 | 0.6 | 39.2 | 29.7 | 0.9 | 58.2 | 54.1 | 1.4 | 73.6 | 59.1 | 2.0 | 88.3 | 58.7 | 2.8 |
| 111In-MH-PC-AB-52 (n=3) | 4.2 | 3.7 | 0.4 | 13.5 | 10.8 | 0.4 | 77.2 | 41.2 | 0.6 | 98.6 | 41.7 | 0.9 | 104.6 | 47.7 | 1.1 | 88.5 | 49.1 | 1.4 |
| 111In-MH-PC-AB-53 (n=3) | 6.5 | 5.0 | 0.2 | 27.3 | 24.3 | 0.3 | 102.8 | 66.2 | 0.5 | 118.8 | 65.6 | 0.8 | 120.0 | 70.9 | 1.2 | 158.3 | 87.2 | 1.7 |
| 111In-MH-PC-AB-56 (n=3) | 3.0 | 2.0 | 0.5 | 4.1 | 3.4 | 0.7 | 35.1 | 25.1 | 2.7 | 88.4 | 74.8 | 5.9 | 140.9 | 110.6 | 9.5 | 150.5 | 121.4 | 13.2 |
| 111In-MH-PC-AB-57 (n=3) | 1.9 | 1.7 | 0.7 | 2.0 | 1.6 | 0.7 | 17.7 | 10.0 | 0.9 | 18.9 | 13.2 | 1.2 | 27.9 | 9.5 | 1.4 | 28.3 | 10.4 | 1.6 |

FIG. 32

PSMA TARGETED RADIOTHERAPY MEDICINE AND PREPARATION METHOD THEREOF

BACKGROUND OF THE INVENTION

1. Field of the Invention

The invention relates to a precursor for labeling a radioisotope for diagnosis and treatment of prostate cancer, in particular to a precursor specific binding with prostate-specific membrane antigen (PSMA) having three variable bases for changing biodistribution and biological half-life, applicable to be labeled with radioisotopes for prostate cancer diagnosis and treatment.

2. Description of Related Art

According to the World Health Organization (WHO) International Agency for Research on Cancer (IARC) GLOBOCAN 2012 statistics on global mortality and prevalence data, prostate cancer ranks fourth in common cancers regardless of gender, ranking second among men's common cancers about 1.1 million men worldwide are diagnosed with prostate cancer. In the WHO sub-region, the prevalence of male prostate cancer in each region was 40% in the WHO European Region, 38% in the WHO Region of the Americas, and 13% in the WHO Western Pacific Region. Africa Region (WHO African Region) 4.2%, Southeast Asia Region (WHO South-East Asia Region) 3.6% and the Eastern Mediterranean Region (WHO Eastern Mediterranean Region) 1.4%.

Prostate-specific membrane antigen (PSMA) is a type 2 membrane glycoprotein. The physiological role of this protein is usually transmembrane protein, membrane receptor or membrane proteolytic enzyme. David A. Silver et al. (1997) confirmed by immunostaining that PSMA is not only expressed in prostate cancer cells, but also in a small number of normal tissues, including renal tubular, duodenal, colon, and benign prostatic tissue. Compared with normal tissue prostate cancer specimens, the proportion of PSMA expression is as high as 100 to 1000 times, and this overexpression is not found in benign prostatic hyperplasia. Bostwick et al. (1998) identified 184 prostate cancer specimens by tissue immunostaining. All specimens showed PSMA and their performance was correlated with cancer severity, indicating that 69.5% of benign epithelial tissues having positive performance, 77.9% of the high-grade cancerous tissues having positive performance, and 80.2% of the malignant tumor tissues having positive performance.

PSMA is structurally identical to the glutamate carboxypeptidase II (GCP II) protein involved in causing neurological disorders and the catalytic activity of the protein is cutting out glutamate from N-acetylaspartyl glutamate and polyglutamated folate.

Therefore, the Tenniswood's team (2003) pioneered the use of lymph node carcinoma of the Prostate (LNCaP, with expressed PSMA) and Du-145 cells without expressed PSMA to demonstrate a phosphate-based GCP II inhibitor as a potential imaging agent for prostate cancer.

Recently published in the International Journal of Nuclear Medicine, Dr. Richard Baum, a scientist from the German Cancer Research Center, said that the German Bad Berka Cancer Center is currently using PSMA small molecules for clinical application and it can be specifically absorbed and labeled by a variety of radionuclides on the PSMA. At present, the tumor uptake rate of related drugs is low, but PSMA seems to be a new target for the diagnosis of prostate cancer and the development of special targeted therapies.

Traditional angiography for prostate cancer relies mainly on rectal ultrasound, CT, and MRI. Like these diagnostic methods, there is no specificity for prostate cancer. For example, clinical prostate biopsy for prostate cancer (PCa) can be guided by transrectal ultrasound (TURS). However, a puncture false negative rate of commonly used TURS six-point system is about 30% with serious complications.

Clinically, non-invasive diagnostic methods for prostate cancer (PCa) include imaging examinations such as digital rectal examination, PSA test, CT, MRI, and radionuclide bone angiography. These methods contribute to the staging of prostate cancer (PCa), but there are also various disadvantages described below. Blood PSA index examination: the blood PSA index is used as a tumor biomarker for prostate cancer (PCa), which is currently widely used as sensitive indicators to diagnose prostate cancer (PCa). However, when the blood PSA index is 4 to 10 µg/L, it is difficult to diagnose prostate cancer (PCa), and the blood PSA index can't reflect the characteristics of clinical pathology, no specificity, and can't effectively distinguish the local tumor lesions or distant metastasis.

Medical imaging diagnosis: Although the general clinical examination of prostate cancer (PCa) by medical imaging is main means, however, CT examination cannot distinguish between cancerous tissue and benign proliferative tissue, so it is not clear whether prostate cancer (PCa) is present. MRI has a higher resolution for soft tissue and is superior to CT and ultrasound in the diagnosis of prostate lesions, which can effectively identify prostate cancer (PCa) and benign prostatic hyperplasia. However, prostate cancer (PCa) is prone to lymph node metastasis and distal bone metastasis, which reduces the value of MRI in the diagnosis and staging of prostate cancer (PCa). Tc-99m-MDP bone angiography can be compared with X-ray examination. It can be found 3 to 6 months ahead of time. It is helpful to determine the accurate clinical stage of prostate cancer (PCa), but its sensitivity is high while specificity is poor. Clinically, approximately 50% of patients with prostate cancer (PCa) have a bone metastasis that die within 30 to 35 months after diagnosis. Therefore, the current imaging and sectioning methods have been difficult to meet the clinical requirements for early diagnosis and accurate staging of prostate cancer (PCa).

At present, nuclear medicine molecular angiography technology has gradually entered the core of clinical cancer diagnosis and treatment, which is described below. F-18-NaF bone angiography: clinical studies have shown that Tc-99m-MDP bone angiography has a sensitivity of 50.8% and a specificity of 82% for prostate cancer (PCa) bone metastasis. In contrast, F-18-NaF PET/CT angiography has a sensitivity of 93% and a specificity of 54%, and it has a higher spatial resolution, and can perform CT anatomical localization and three-dimensional imaging, which is expected to be an early discovery in clinical imaging examination of prostate cancer (PCa) bone metastasis. Although F-18-NaF can find more metastases, it does not change the clinical treatment plan.

F-18-FDG angiography: F-18-FDG PET/CT can provide effective clinical data for early diagnosis, staging, protocol optimization, and prognosis evaluation of prostate cancer (PCa). However, similar to normal cells, prostate cancer (PCa) Glut expression level is low, it is difficult to distinguish benign lesions, and F-18-FDG is mainly excreted by the urinary system, which will interfere with the diagnosis of prostate cancer (PCa), resulting in F-18-FDG a low detection rate for prostate cancer (PCa) and limited diagnostic value.

C-11-Choline angiography: C-11-Choline prostate cancer (PCa) has a significant contrast advantage compared with F-18-NaF. C-11-Choline can be concentrated in tumor cells and retained in cells after being phosphorylated in tumor cells. The diagnostic ability of C-11-Choline PET for prostate cancer (PCa) is better than that of F-18-FDG with a positive rate of 47%, and F-18-NaF is only 27%. The sensitivity of N-[F-18]fluoromethyl choline (F-18-fluoromethylcholine, F-18-FECH) is 84.7%, and the specificity is 91.1%, indicating that the sensitivity and specificity of tumor diagnosis for C-11/F-18-FECH are significantly better than that of Tc-99m-MDP and F-18-NaF. Yamaguchi (Eur J Nucl Med Mol Imaging. 2005) and other scholars compared the sensitivity of C-11-Choline PET with MRI-targeted primary prostate cancer (PCa) and found that C-11-Choline-PET sensitivity is close to 100%, while MRI is only 60%. However, C-11-Choline angiography is not effective in identifying primary lesions of prostate cancer (PCa).

F-18-FACBC (anti-1-amino-3-F-18-fluorocyclobutane-1-carboxylic acid) angiography: F-18-FACBC is an L-type amino acid transporter 1 and alanine, serine and cysteine, and the matrix of the acid transporter is hardly excreted by the kidneys, so the pelvis can be clearly developed and can be used for the detection of prostate cancer (PCa).

16β-F-18-fluoro-5-dihydrotestosterone (F-18-DHT) androgen receptor imaging: In prostate tissue, DHT is the major androgen and Its concentration is 5 times that of testosterone, and its affinity with androgen receptor is 10 times that of testosterone. F-18-DHT has a high ratio of prostate to soft tissue radioactivity and is expected to be used in the diagnosis, staging, prognosis and evaluation of hormone therapy effects of prostate cancer (PCa). Using F-18-DHT as a molecular probe, PET and MR were simultaneously used for the diagnosis and treatment of prostate cancer (PCa), and the clinical application of F-18-DHT probe in the diagnosis and treatment of prostate tumor hormone was promoted.

A novel molecular probe targeting prostate specific membrane antigen (PSMA): With the deepening of molecular biology research, PSMA receptors are an ideal target for molecular imaging and targeted therapy of prostate cancer (PCa). Depending on the drugs, which include monoclonal antibodies (abbreviated to monoclonal antibodies), peptides, and small molecules, and PSMA sites of action, PSMA targeting antibodies are divided into intracellular domain antibodies (such as 7EI1, PM2J004.5) and extracellular domain antibodies (such as J591, J415, PEQ226.6).

In the above-mentioned diagnostic methods including F-18-FDG, some cases cannot judge prostate cancer, especially in the case of metastasis. The current study found that prostate cancer cells surface highly expressed prostate specific membrane antigen (PSMA), so as long as anti-PSMA can be developed, the relevant radioactive nuclear medicine can be developed. A variety of antibodies, such as PSMA-11, have been developed and can be diagnosed using the Ga-68 marker.

However, clinical progress has moved toward the PRLT (PSMA-targeted Radioligand Therapy) concept, and it is hoped that the diagnosis will be synchronized. On the other hand, treatment after diagnosis often results in a decline in quality of life or poor outcome, especially after metastatic prostate cancer. Therefore, the development of radionuclides for the treatment of prostate and metastatic cancer has a high degree of urgent need for clinicians in treatment of various stages of prostate cancer.

SUMMARY OF THE INVENTION

There are a large number of NAAG inhibitors have been developed and mainly used in diagnosis, which was based on urea-based structure.

In urea-based NAAG inhibitors, there is only PSMA-617 can be used for the treatment with Lu-177 labeled.

At present, the drug has entered the clinical phase III and is expected to be completed in 2020. The current clinical results show that in addition to the efficacy, it can increase the quality of life of the patient. But because the drug has a half-life of 10.8 hours and the patient takes about 4 times in the overall course of treatment that will spend more time and money. With references and our past experiences in drug design, we made improvement on the basis of PSMA-617 with adding 3 changes, extending its residence time in the blood, increasing the discharge half-life, and achieving the goal of treatment with fewer injections.

The PSMA receptor is expressing in prostate cancer, and the MH-PC-AB-X has a high binding affinity with the PSMA receptor that can be used as a diagnostic or therapeutic drug precursor for prostate cancer.

The present invention uses MH-PC-AB-X as the backbone to synthesize a series of theranostics agents that could label with radionuclides, including (1) radioisotopes, (2) metal chelating agent, (3) three changeable moiety, (4) radiolabeling method and quality control methods.

The preparation steps include (1) MH-PC-AB-X series compound synthesis method; (2) the radiolabeling of MH-PC-AB-X series compounds with radionuclides Ga-67, Ga-68, Cu-64, In-111, Y-90 and Lu-177; (3) the amount peptide of radiolabeling of MH-PC-AB-X with radionuclides such as Ga-68, Ga-67, In-111, Y-90 and Lu-177, the use of the peptide dosage is about 20 μg, the reaction temperature is 95° C., the pH value of the reaction buffer is 3.7, 4.7 or 6.0, the labeling time is 10 to 15 minutes, and the labeling efficiency can reach 95%. and its binding ability has been demonstrated in LNCaP (PSMA positive) prostate cancer tumor animal model.

The PSMA targeted radiotherapy medicine of the present invention is characterized by the novelty of MH-PC-AB-X. The labeling is convenient without purification by other columns. The labeling efficiency can reach more than 95%. It is known from tumor animal experimental data that it has high binding to tumor. Significant tumor accumulation images can be seen in prostate cancer (PCa) animal model (PSMA+) in only 2 to 4 hours, which is different from the PSMA-617 characteristics recited in the literature. In particular, the MH-PC-AB-X of the present invention maintains a high accumulation amount up to 48 hours.

BRIEF DESCRIPTION OF THE DRAWINGS

FIG. 15 shows Ga-68-MH-PC-NAB-1 labeling conditions and quality control analysis table

FIG. 19 shows In-111-MH-PC-AB-9 marking condition and quality control analysis table

FIG. 22 shows In-111-MH-PC-AB-52 labeling conditions and quality control analysis table

FIG. 25 shows In-111-MH-PC-AB-53 marking conditions and quality control analysis table

FIG. 29 shows Ga-68-MH-PC-AB-X organ distribution FIG. 32 shows In-111-MH-PC-AB-X organ distribution

DETAILED DESCRIPTION OF THE PREFERRED EMBODIMENTS

The P1, P2 and P3 positions of the PSMA inhibitor MH-PC-AB-X structure of the present invention are indicated below:

TABLE 1

| No | P1 | P2 | P3 |
|---|---|---|---|
| 1 | | | |
| 2 | | | |

TABLE 1-continued

| No | P1 | P2 | P3 |
| --- | --- | --- | --- |
| 3 | (diaminopropionic acid derivative with N-acyl 4-(p-tolyl)butanamide side chain) | 4-aminophenylalanine | 4-aminophenylalanine |
| 4 | (diaminobutyric acid derivative with N-acyl 4-(p-tolyl)butanamide side chain) | 4-bromophenylalanine | 4-bromophenylalanine |
| 5 | (ornithine/lysine derivative with N-acyl 4-(p-tolyl)butanamide side chain) | 4-iodophenylalanine | 4-iodophenylalanine |

TABLE 1-continued

| No | P1 | P2 | P3 |
|----|----|----|----|
| 6  | (lysine with N-ε-acyl group bearing 4-methylphenylpropyl chain) | (4-chlorobenzyl amino acid) | (4-chlorobenzyl amino acid) |
| 7  | (lysine analog with β-hydroxy and N-acyl 4-methylphenylpropyl chain) | (4-methylbenzyl amino acid) | (4-methylbenzyl amino acid) |
| 8  | (blank) | (4-(HO₃SCH₂)-benzyl amino acid) | (4-(HO₃SCH₂)-benzyl amino acid) |
| 9  | (blank) | (4-fluorobenzyl amino acid) | (4-fluorobenzyl amino acid) |
| 10 | (blank) | (4-nitrobenzyl amino acid) | (4-nitrobenzyl amino acid) |

TABLE 1-continued
| No | P1 | P2 | P3 |
|----|----|----|----|
| 11 | (blank) | 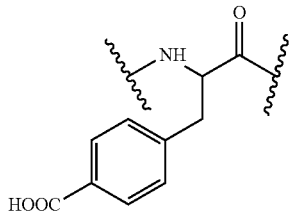 [SMILES: *NC(Cc1ccc(C(=O)O)cc1)C(*)=O] | 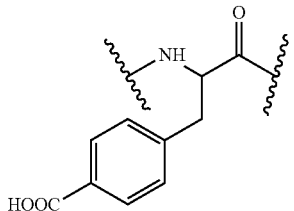 [SMILES: *NC(Cc1ccc(C(=O)O)cc1)C(*)=O] |
| 12 | (blank) | 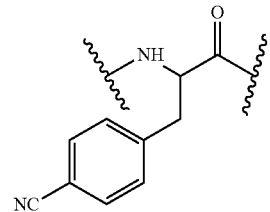 [SMILES: *NC(Cc1ccc(C#N)cc1)C(*)=O] | 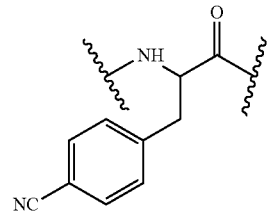 |
| 13 | (blank) | 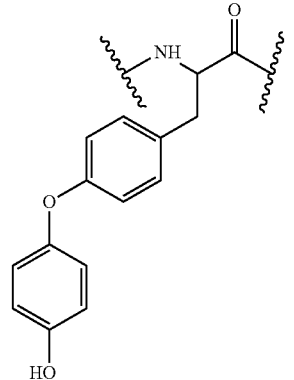 [SMILES: *NC(Cc1ccc(Oc2ccc(O)cc2)cc1)C(*)=O] | 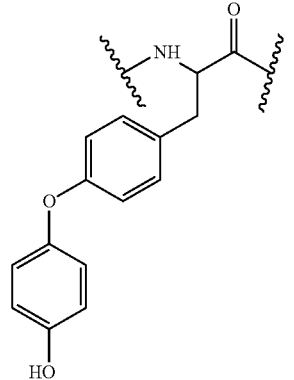 [SMILES: *NC(Cc1ccc(Oc2ccc(O)cc2)cc1)C(*)=O] |
| 14 | (blank) | 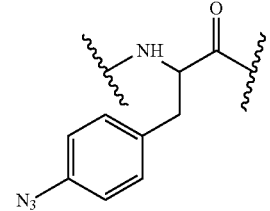 [SMILES: *NC(Cc1ccc(N=[N+]=[N-])cc1)C(*)=O] | 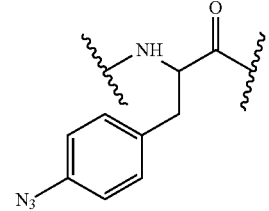 [SMILES: *NC(Cc1ccc(N=[N+]=[N-])cc1)C(*)=O] |
| 15 | (blank) | 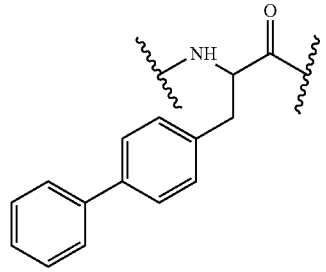 [SMILES: *NC(Cc1ccc(-c2ccccc2)cc1)C(*)=O] | 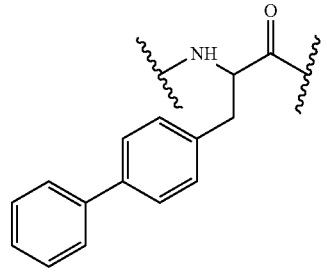 [SMILES: *NC(Cc1ccc(-c2ccccc2)cc1)C(*)=O] |

TABLE 1-continued
| No | P1 | P2 | P3 |
|---|---|---|---|
| 16 | (blank) | 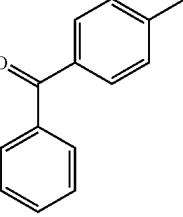 | 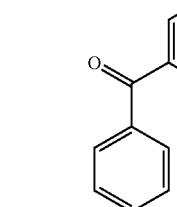 |
| 17 | (blank) | 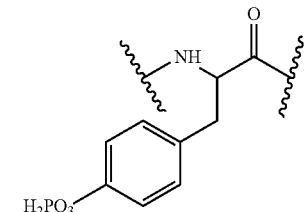 | 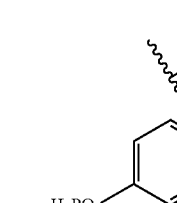 |
| 18 | (blank) | 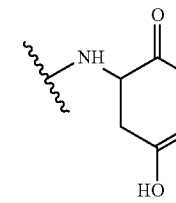 | 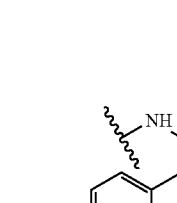 |
| 19 | (blank) | 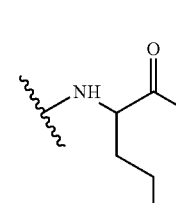 | 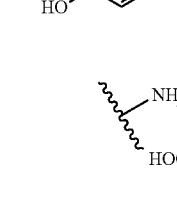 |
| 20 | (blank) | 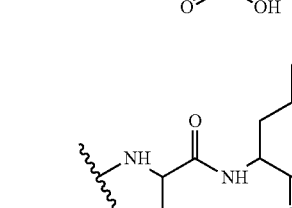 | 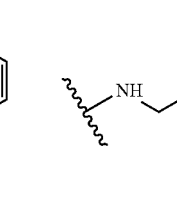 |
| 21 | (blank) | 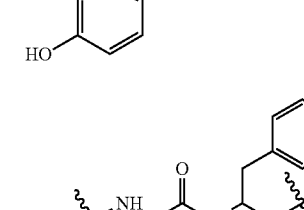 | 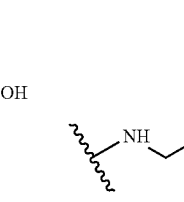 |

TABLE 1-continued

| No | P1 | P2 | P3 |
|----|----|----|----|
| 22 | (blank) | (structure: NH-CH2-C(=O)) | (structure: NH-CH(CH2CH2CH2CH2NH2)-C(=O)) |
| 23 | (blank) | (structure: NH-CH(CH2OH)-C(=O)) | (structure: NH-CH(CH2CH2CH2NH-C(=NH)NH2)-C(=O)) |

Figure 1:
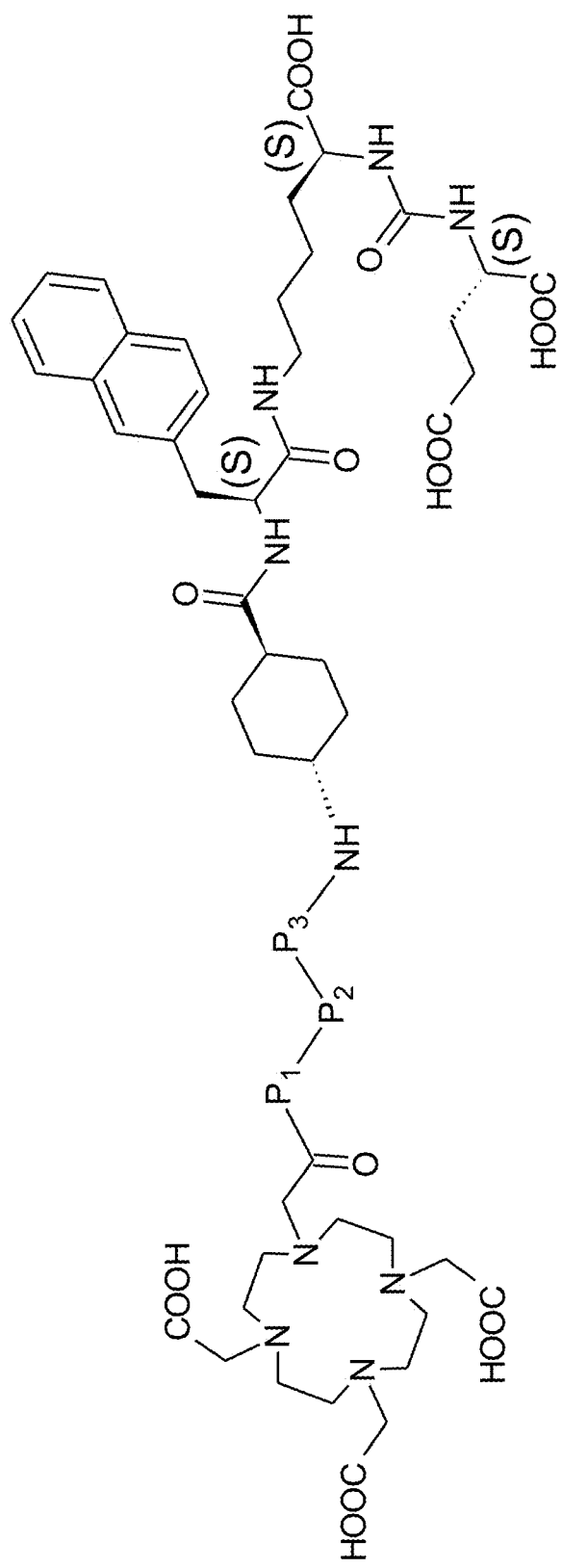
FIG. 1 shows PSMA inhibitor MH-PC-AB-X structural framework
Figure 2:
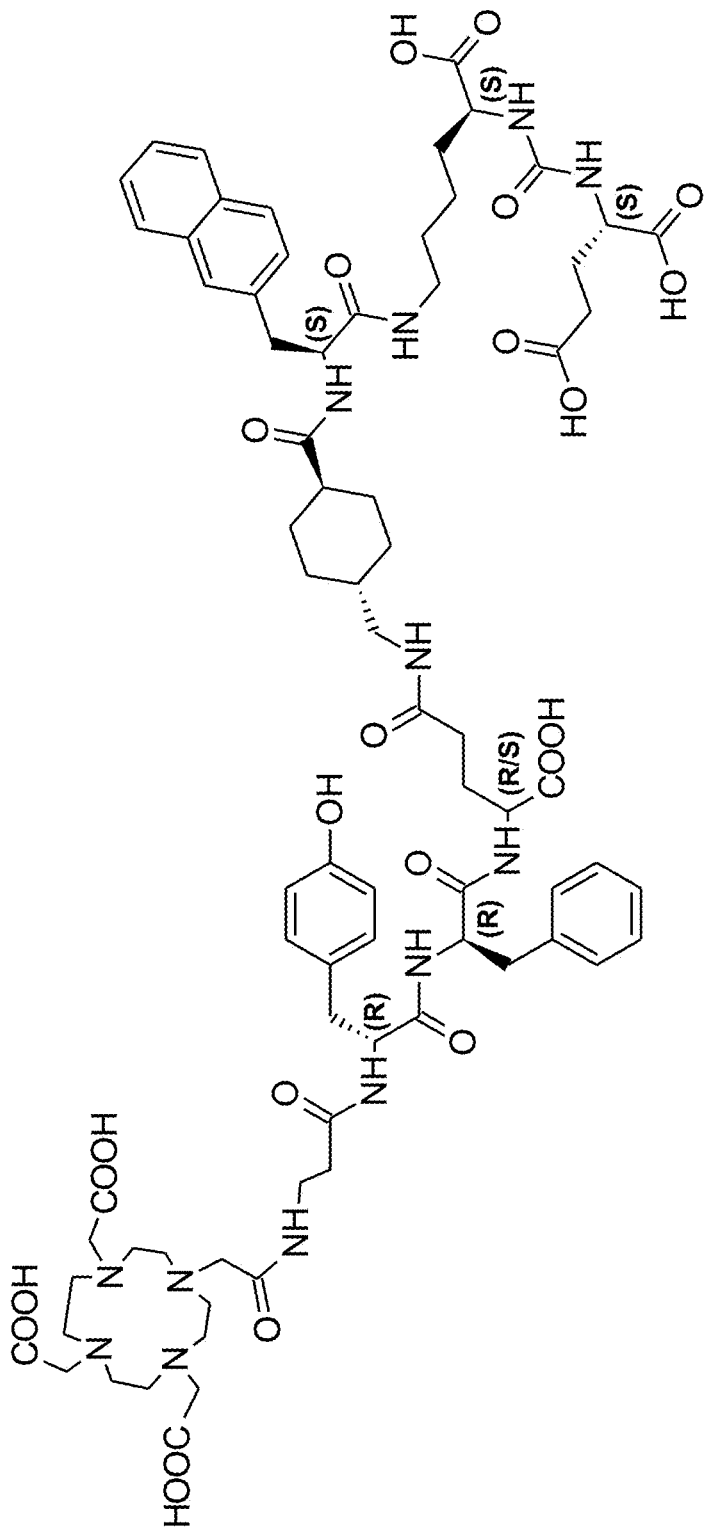
FIG. 2 shows PSMA inhibitor MH-PC-NAB-1 structure

The PSMA inhibitor MH-PC-NAB-1 of the present invention, as shown in FIG. 2, is a structure in which P1-1, P2-20 and P3-19 are combined in the MH-PC-AB-X framework, wherein the two optical structures of P2-20 are R configuration, and P3-19 is R configuration or S configuration.

Figure 3:
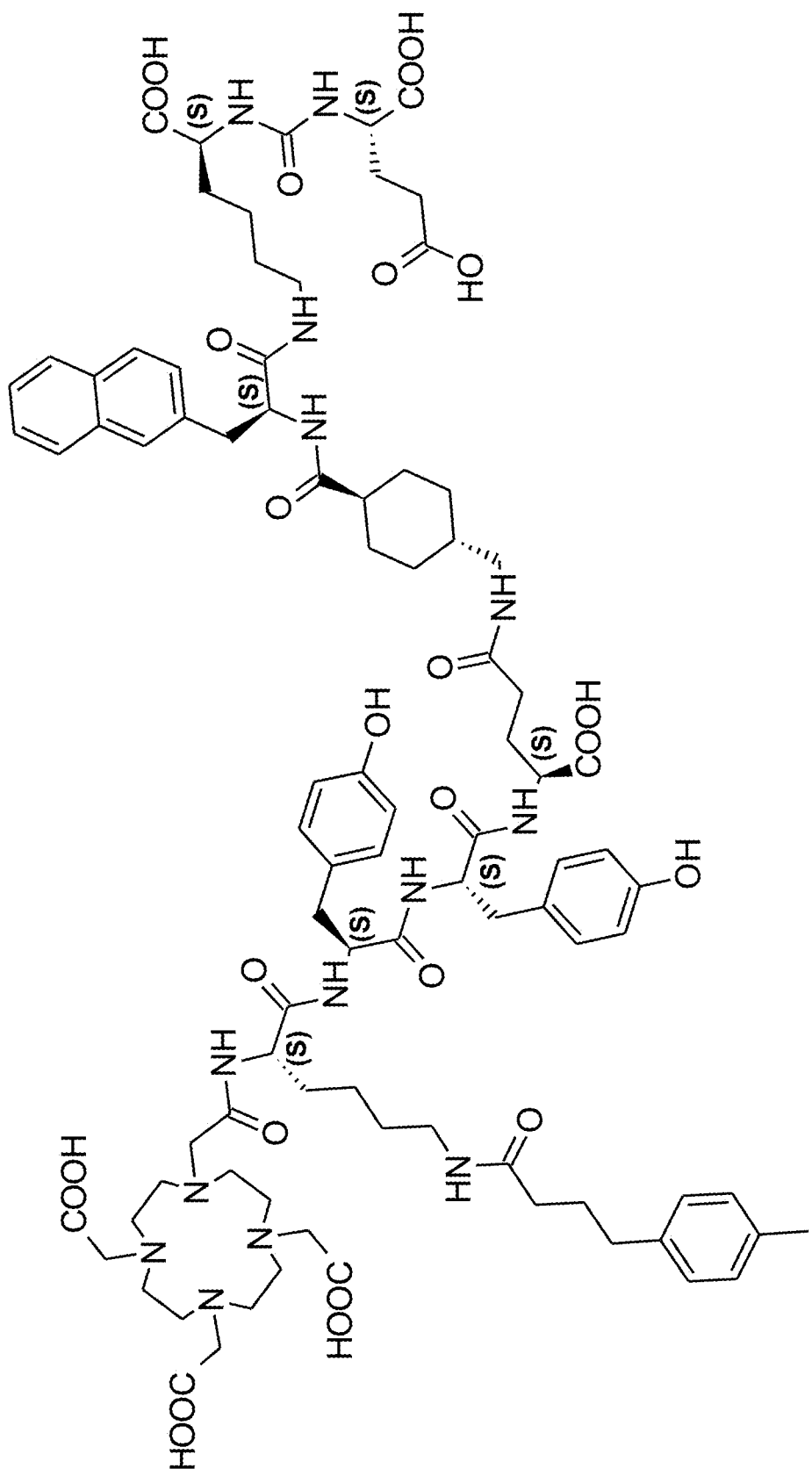
FIG. 3 shows PSMA inhibitor MH-PC-AB-9 structure

The PSMA inhibitor MH-PC-AB-9 of the present invention, as shown in FIG. 3, is a structure in which P1-6, P2-21 and P3-19 are combined in the MH-PC-AB-X framework, wherein the optical structure P1-6, both P2-21 and P3-19 are S configuration.

Figure 4:
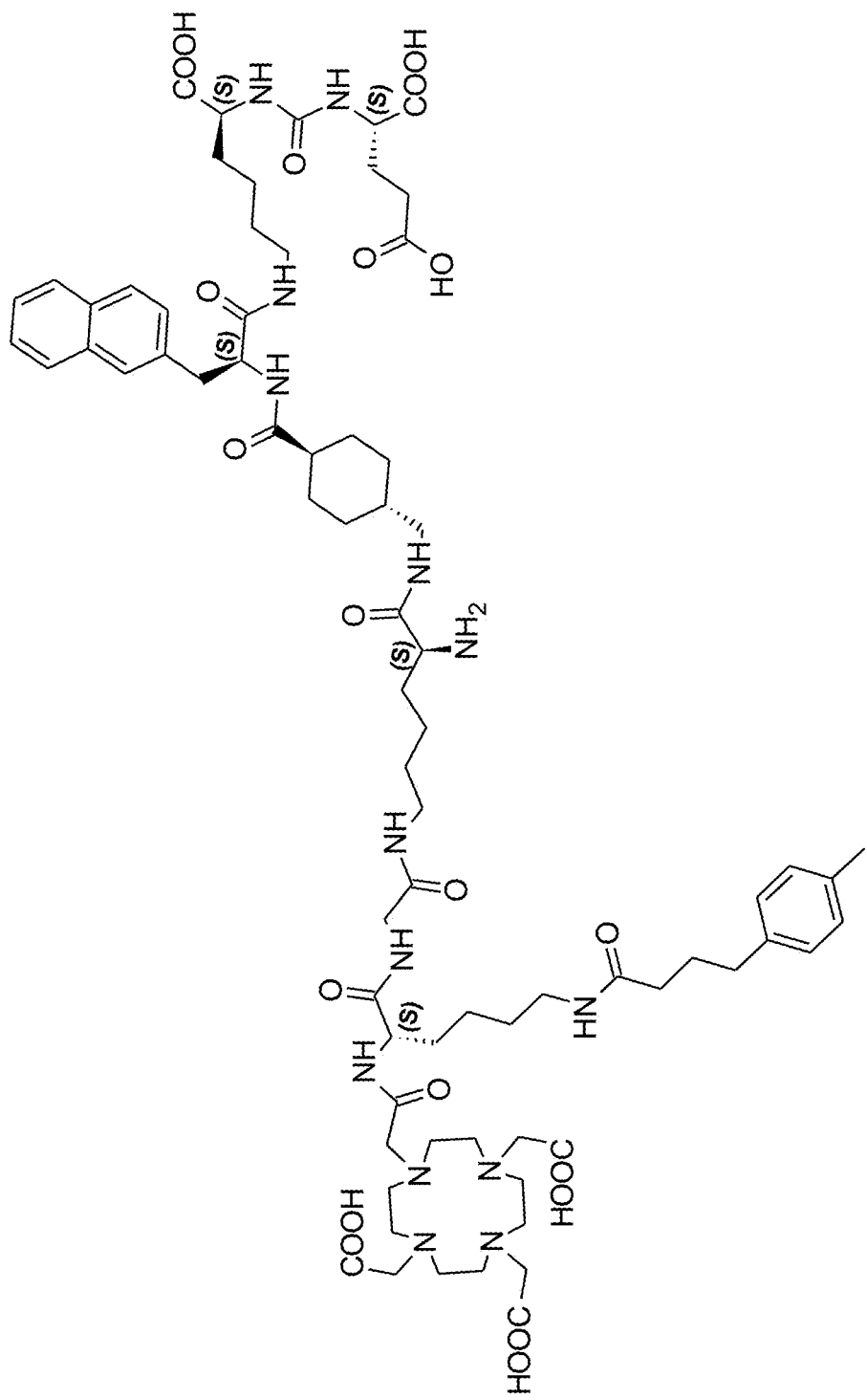
FIG. 4 shows MH-PC-AB-52 structure diagram

The MH-PC-AB-52 of the present invention, as shown in FIG. 4, is a structure in which P1-6, P2-22 and P3-20 are combined in the MH-PC-AB-X framework, wherein the optical structures P1-6 and P3-19 All are S configuration.

Figure 5:
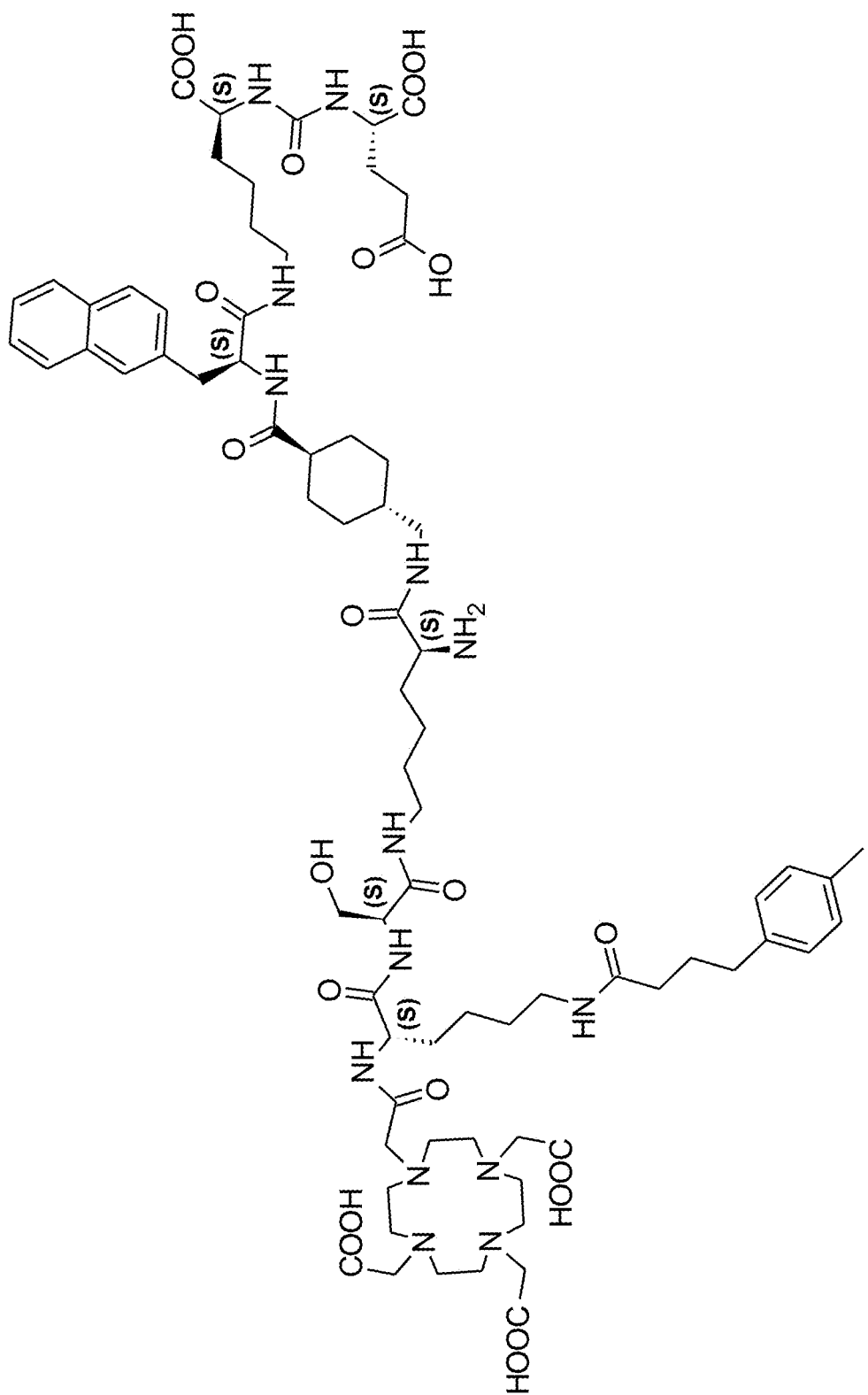
FIG. 5 shows MH-PC-AB-53 structure diagram

The MH-PC-AB-53 of the present invention, as shown in FIG. 5, is a structure in which P1-6, P2-23 and P3-20 are combined in the framework of MH-PC-AB-X, wherein the optical structures P1-6 and P2-23 And P3-20 are S configuration. P1-6, P2-23 and P3-20 are S configuration.

Figure 6:
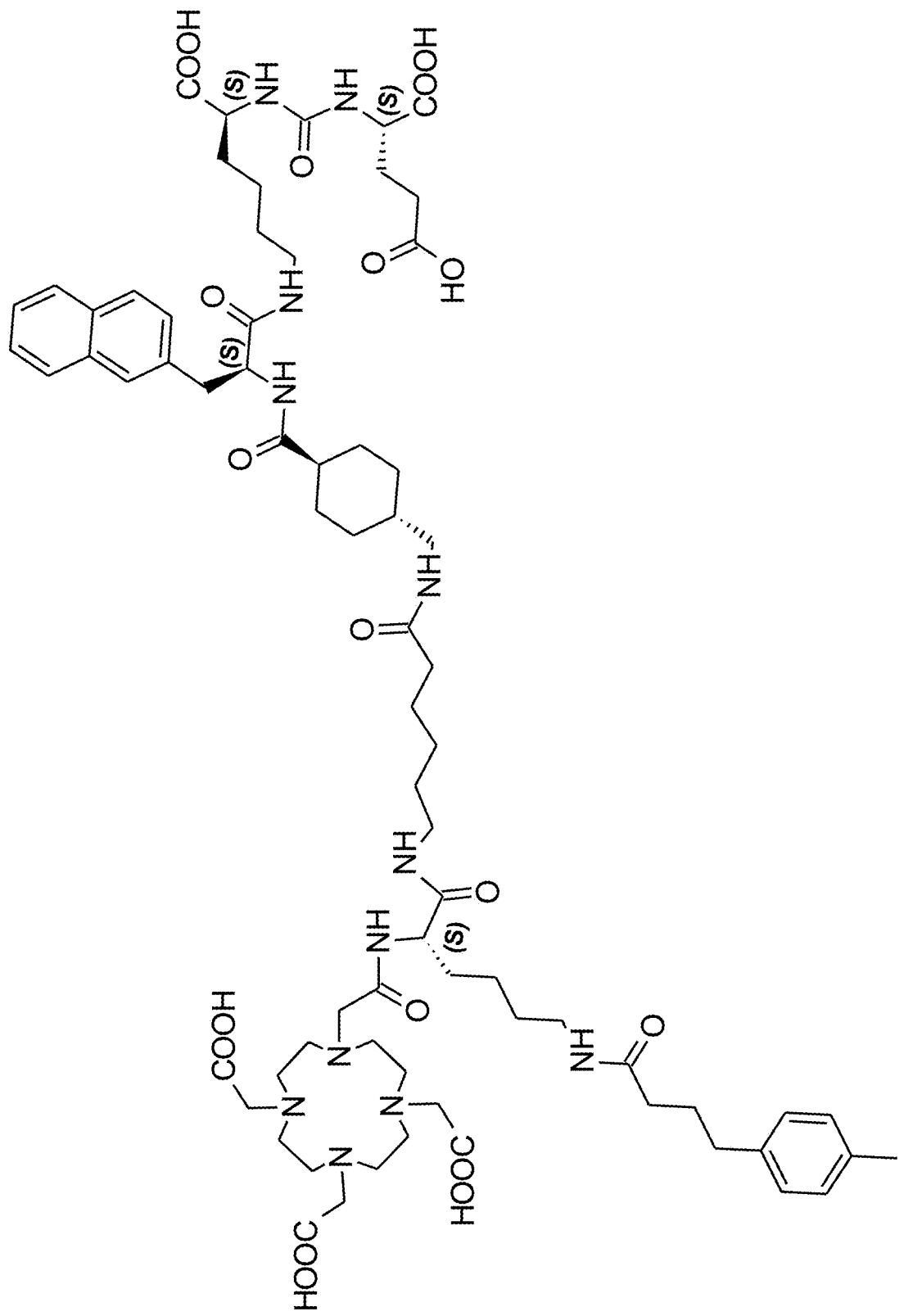
FIG. 6 shows MH-PC-AB-56 structure diagram

The MH-PC-AB-56 of the present invention, as shown in FIG. 6, is a structure in which P3-21 binds in the MH-PC-AB-X framework.

Figure 7:
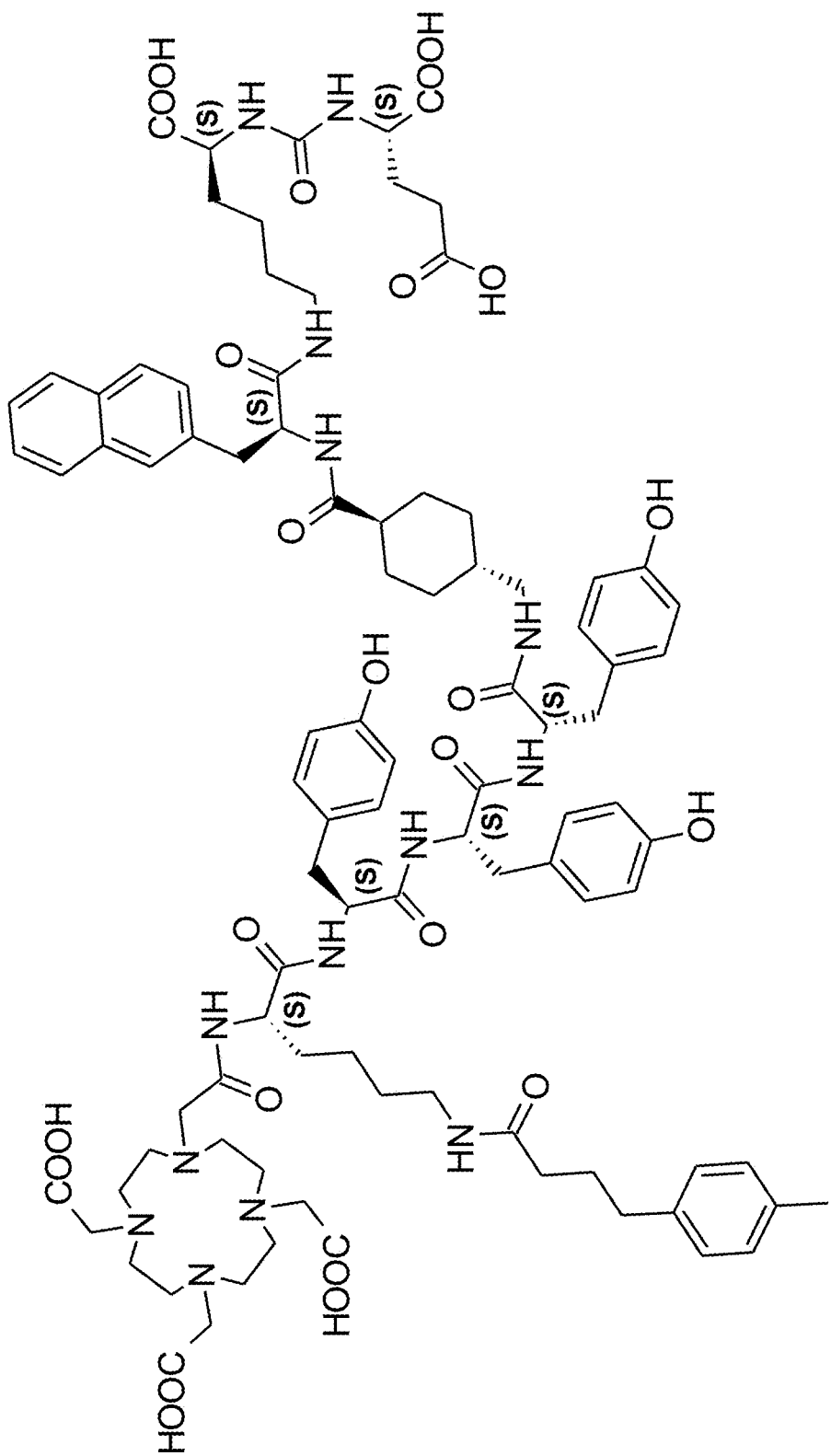
FIG. 7 shows MH-PC-AB-57 structure diagram

The MH-PC-AB-57 of the present invention, as shown in FIG. 7, is a structure of P1-6, P2-1 and P3-13, or P1-6, P2-20 and P3-1, in the framework of MH-PC-AB-X, wherein the optical structures P1-6, P2-1, P2-20, P3-13, and P3-1 are all S configuration.

Designed with MH-PC-AB-X structural frame, MH-PC-NAB-1, MH-PC-AB-1, MH-PC-AB-9, MH-PC-AB-52, MH-PC-AB-53, MH-PC-AB-56 and MH-PC-AB-57, which can be used as a main body of radioactive diagnosis and treatment, combined with radioisotopes such as Ga-68, Ga-67, Cu-64, In-111, Lu-177 or Y-90, are used in the diagnosis and treatment of PSMA expressed prostate cancer (PCa).

Embodiment 1—MH-PC-AB-X Chemical Synthesis Flow Chart from FIG. 8 to FIG. 13A, 13B (Scheme 1 to Scheme 6)

Figure 8:
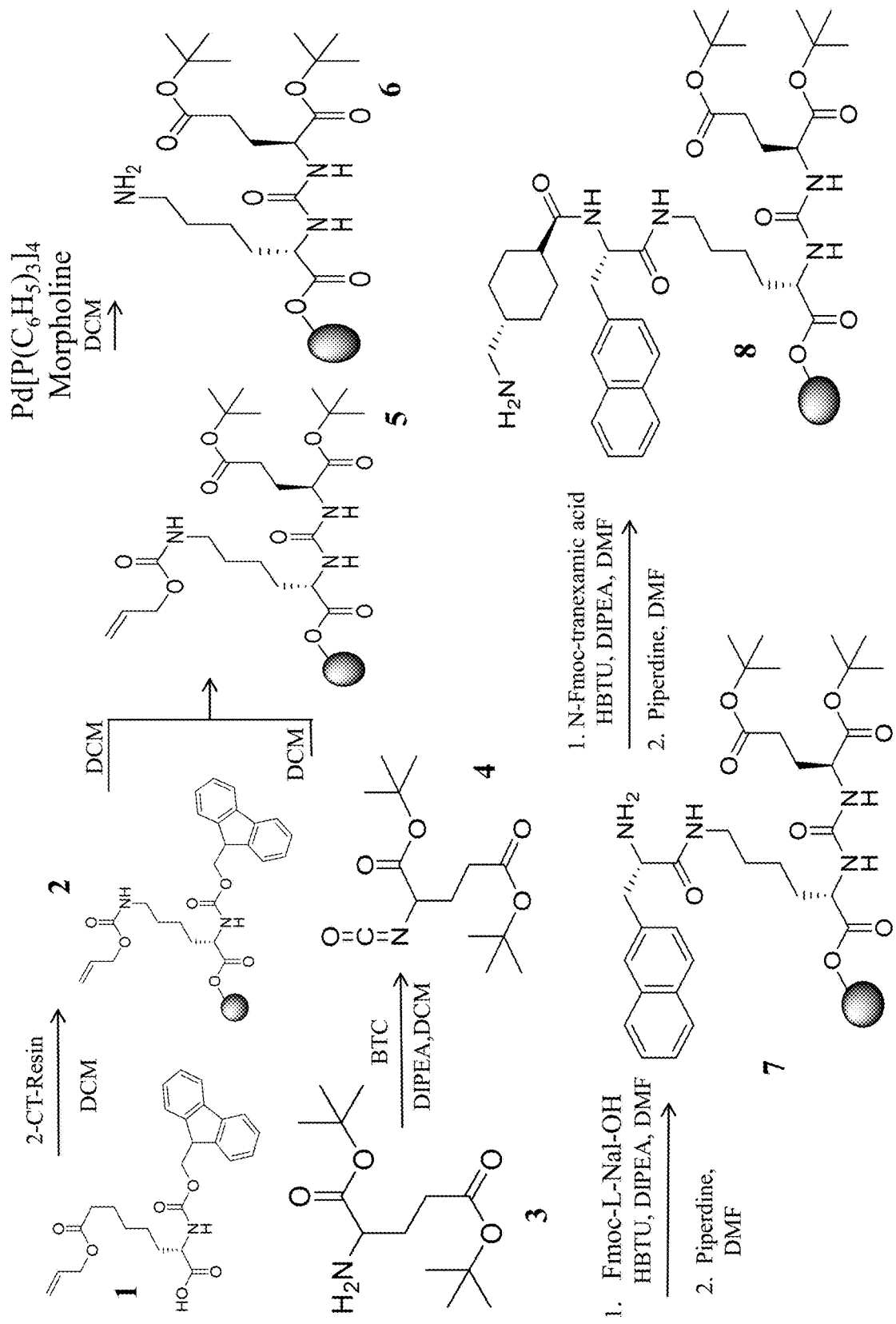
FIG. 8 shows PSMA inhibitor MH-PC-AB-X chemical synthesis processes (1)

Compound 1 of the amine acid derivative and 2-chlorotrityl resin were reacted in dichloromethane at room temperature for 2 hours to obtain compound 2. Compound 3 of the glutamic acid derivative was ice-bathed in dichloromethane for 10 minutes, and a triphosgene reaction was added thereto to stir at 0° C. for 6 hours to obtain an isocyanate compound 4. The compound 2 and the compound 4 were stirred at room temperature for 16 hours to carry out coupling to obtain the compound 5. The compound 5, tetrakis (triphenylphosphine) palladium and morpholine were stirred at room temperature for 3 hours in dichloromethane to remove the allyloxy protecting group to give the compound 6. The chloro-3-(2-naphthalene)-L-amino acid, HBTU, DIPEA and compound 6 were stirred at room temperature for 16 hours to give compound 7. The tranexamic acid derivative, HBTU, DIPEA and compound 7 were stirred at room temperature for 16 hours to give intermediate 8 (FIG. 8).

Figure 9A:
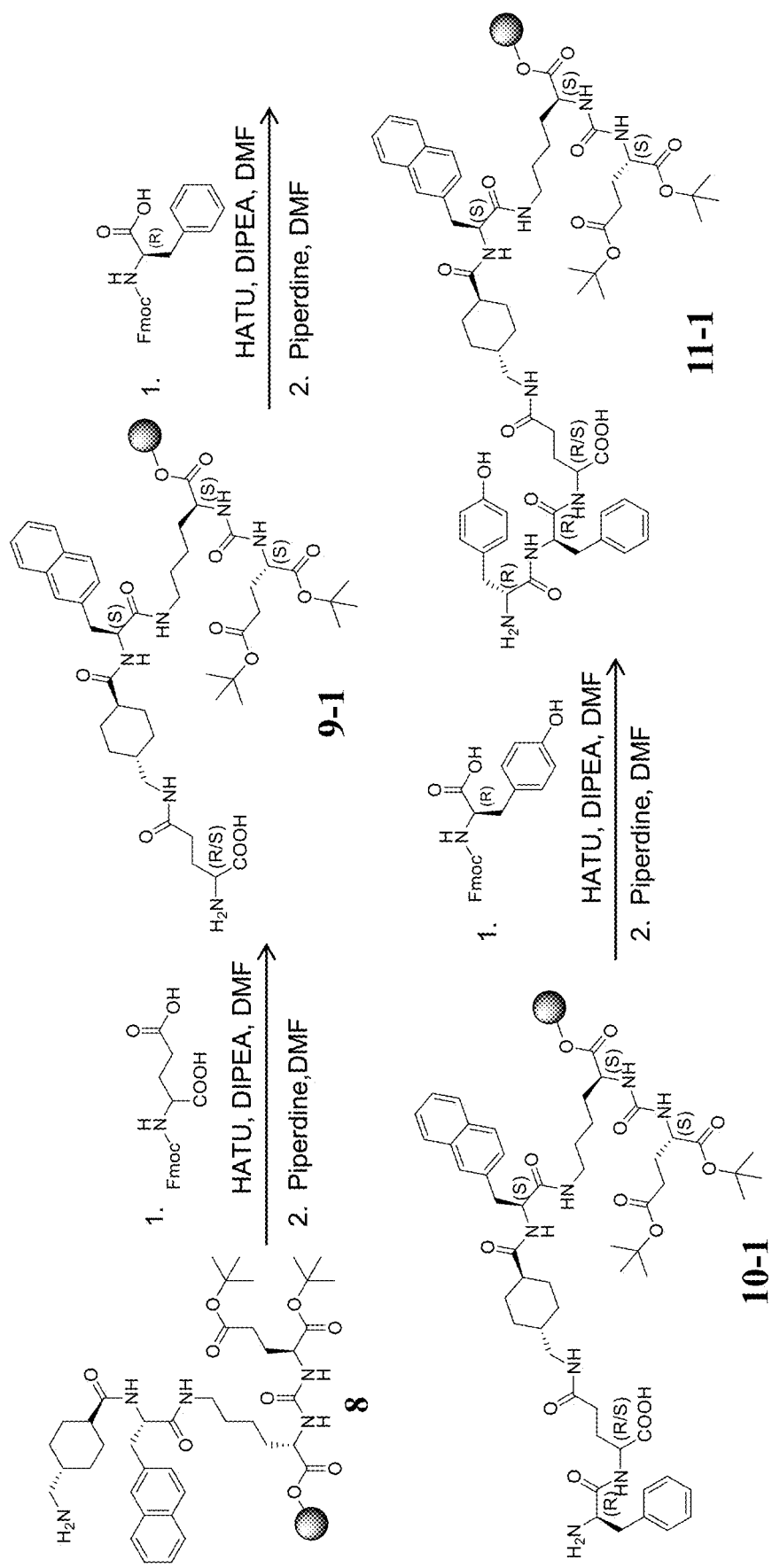
FIG. 9A, 9B shows PSMA inhibitor MH-PC-AB-X chemical synthesis process (2)
Figure 9B:
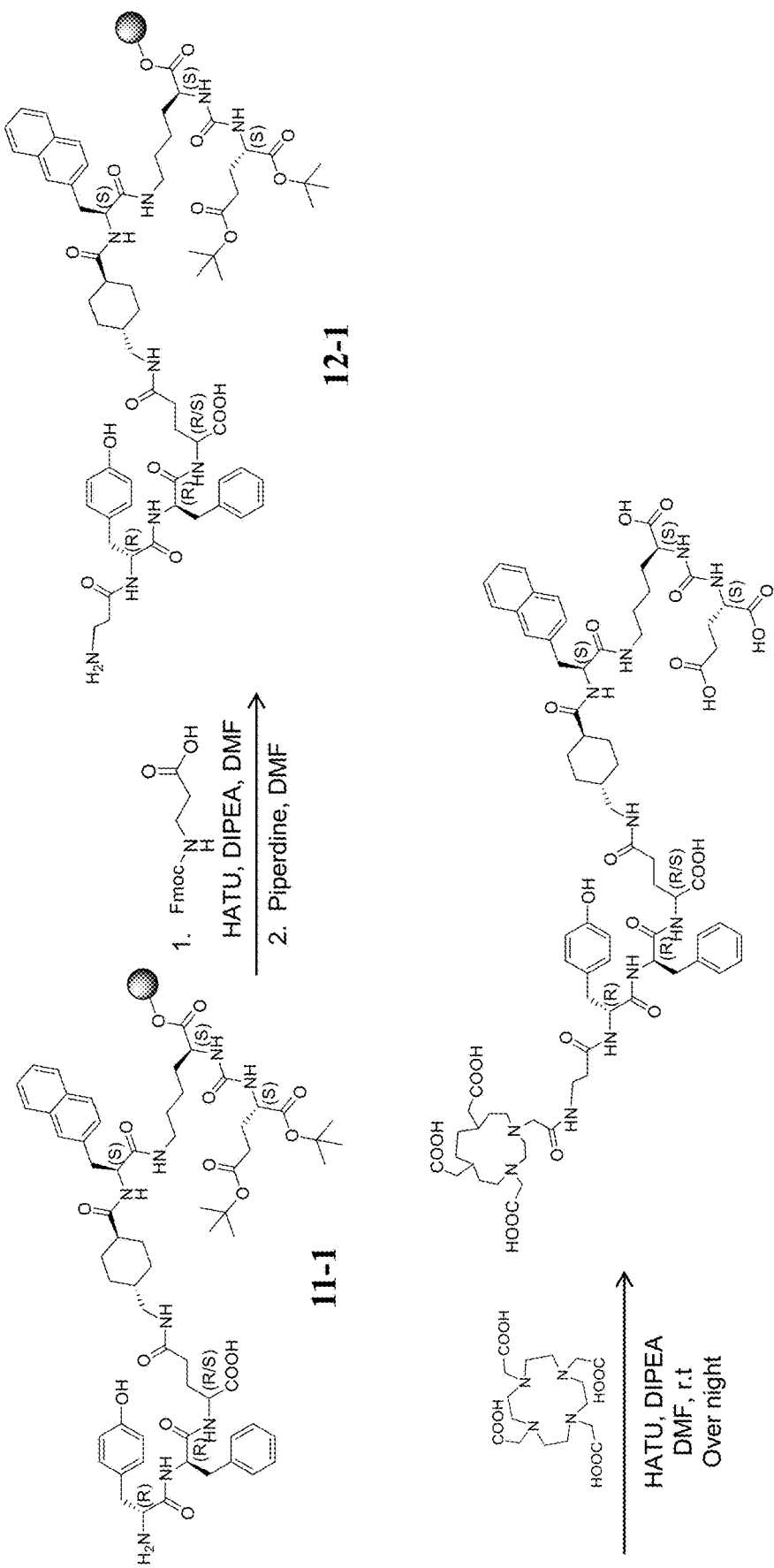

Fmoc-β-Ala-OH, HATU, DIPEA and intermediate 8 were stirred at room temperature for 6 hours in DMF, and then piperidine was added for 4 hours to obtain compound 9-1. Fmoc-Phe-OH, HATU, DIPEA and compound 9-1 were stirred at room temperature for 6 hours and then piperidine was added for 4 hours to obtain compound 10-1. Fmoc-Ser-OH, HATU, DIPEA and compound 10-1 were stirred at room temperature for 6 hours and then piperidine was added for 4 hours to obtain compound 11-1. Fmoc-β-Ala-OH, HATU, DIPEA and compound 11-1 were stirred at room temperature for 6 hours, and then piperidine was added for 4 hours to obtain compound 12-1. After DOTA, HATU, and DIPEA were pre-stirred in DMF for 15 minutes, the compound 12-1 was added to the reaction at room temperature overnight, and then stirred at room temperature for 2 hours in a solvent of trifluoroacetic acid to obtain MH-PC-NAB-1 (FIG. 9A, 9B).

Figure 10A:
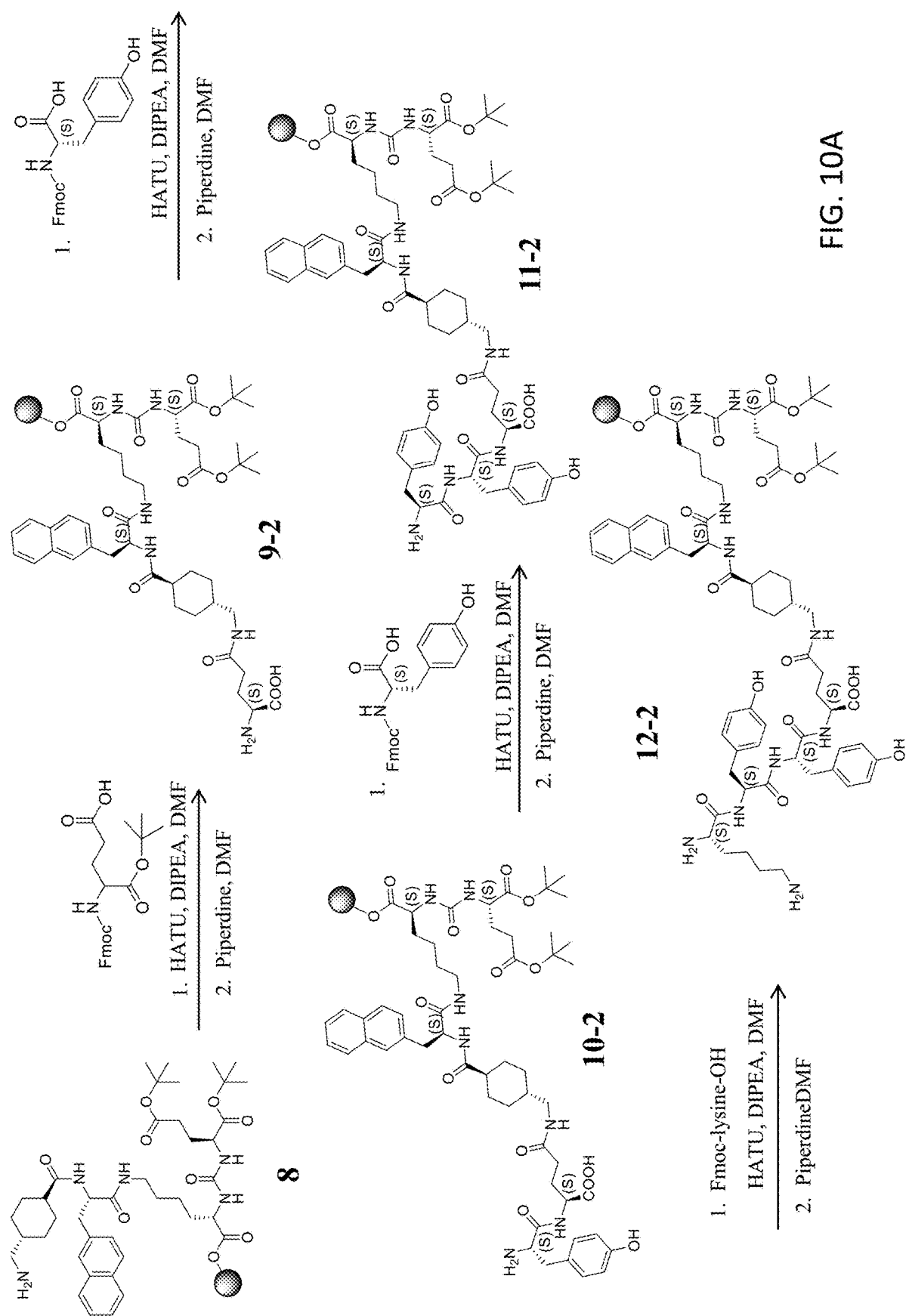
FIG. 10A, 10B shows PSMA inhibitor MH-PC-AB-X chemical synthesis process (3)
Figure 10B:
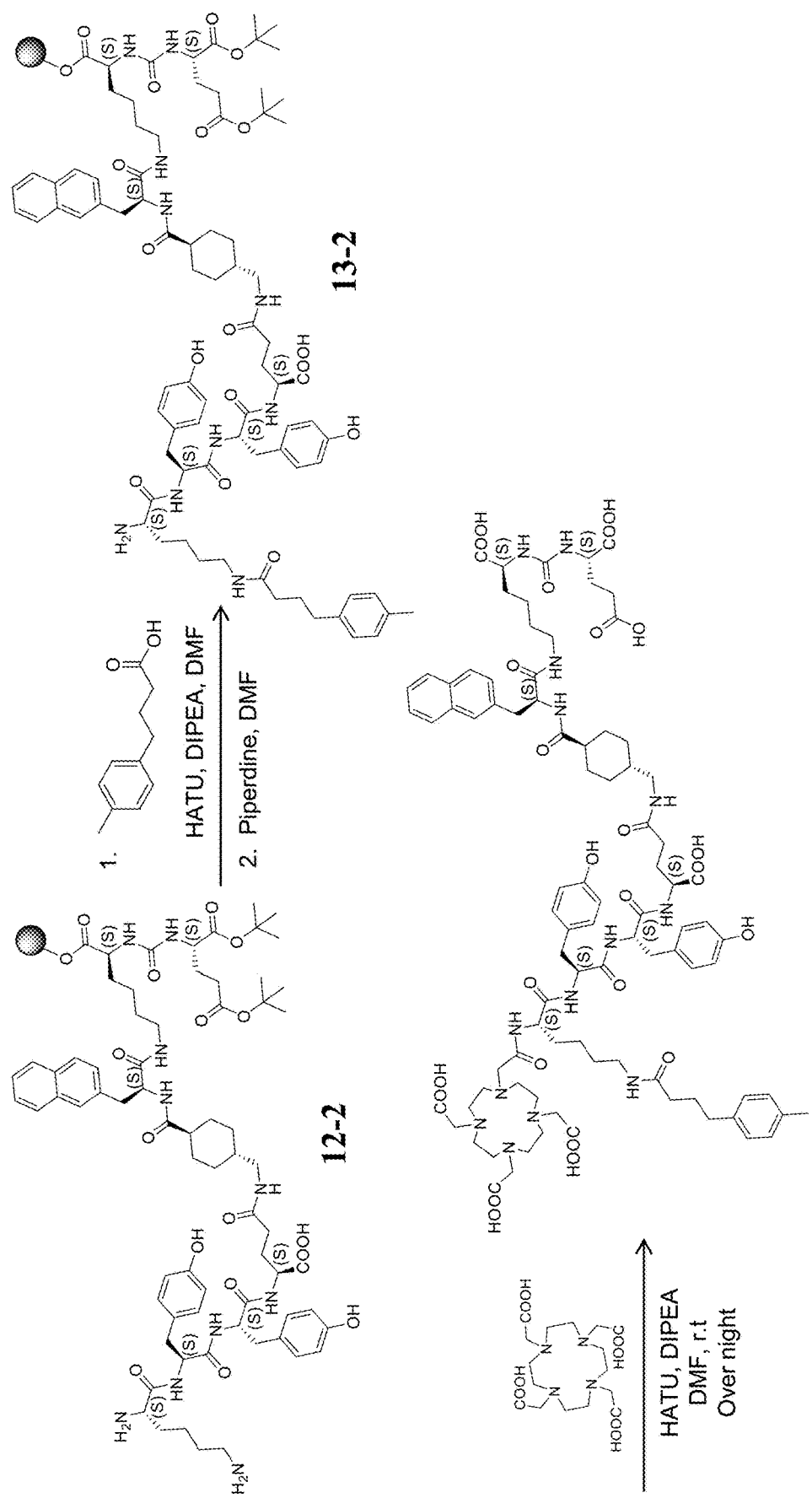

Fmoc-Glu-OH, HATU, DIPEA and Intermediate 8 were stirred at room temperature for 6 hours in DMF, and then piperidine was added for 4 hours to obtain compound 9-2. Fmoc-Ser-OH, HATU, DIPEA and compound 9-2 were stirred at room temperature for 6 hours and then piperidine was added for 4 hours to obtain compound 10-2. Fmoc-Ser-OH, HATU, DIPEA and compound 10-2 were stirred at room temperature for 6 hours and then piperidine was added for 4 hours to obtain compound 11-2. Fmoc-Lysine-OH, HATU, DIPEA and compound 11-2 were stirred at room temperature for 6 hours and then piperidine was added for 4 hours to obtain compound 12-2. The benzene ring derivative, HATU, DIPEA and compound 12-2 were stirred at room temperature for 6 hours, and then piperidine was added for 4 hours to obtain a compound 13-2. After DOTA, HATU, and DIPEA were pre-stirred in DMF for 15 minutes, the compound 13-2 was added to the reaction at room temperature overnight, and then stirred at room temperature for 2 hours in a solvent of trifluoroacetic acid to obtain MH-PC-AB-9 (FIG. 10A, 10B).

Figure 11A:
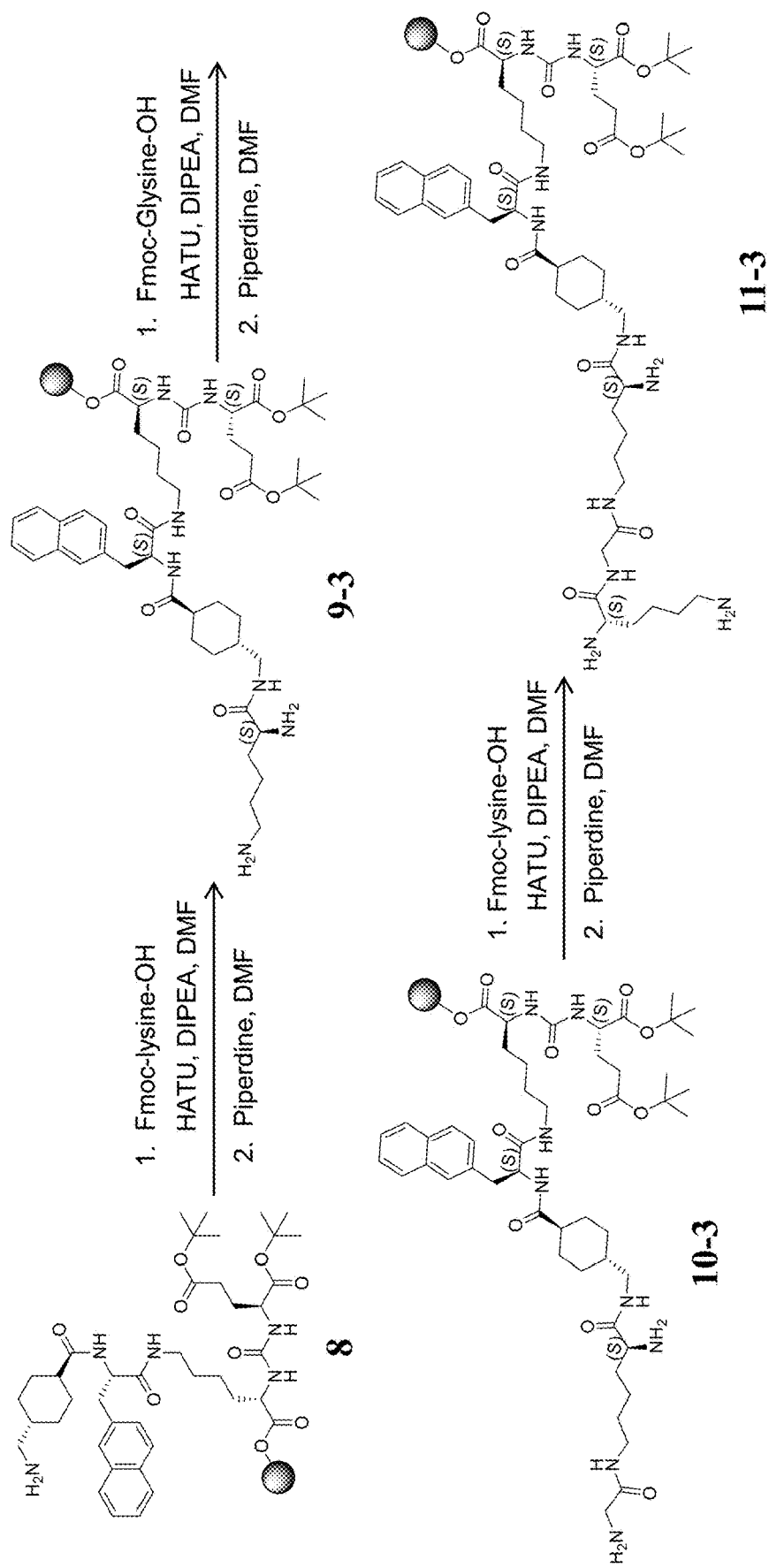
FIG. 11A, 11B shows PSMA inhibitor MH-PC-AB-X chemical synthesis process (4)
Figure 11B:
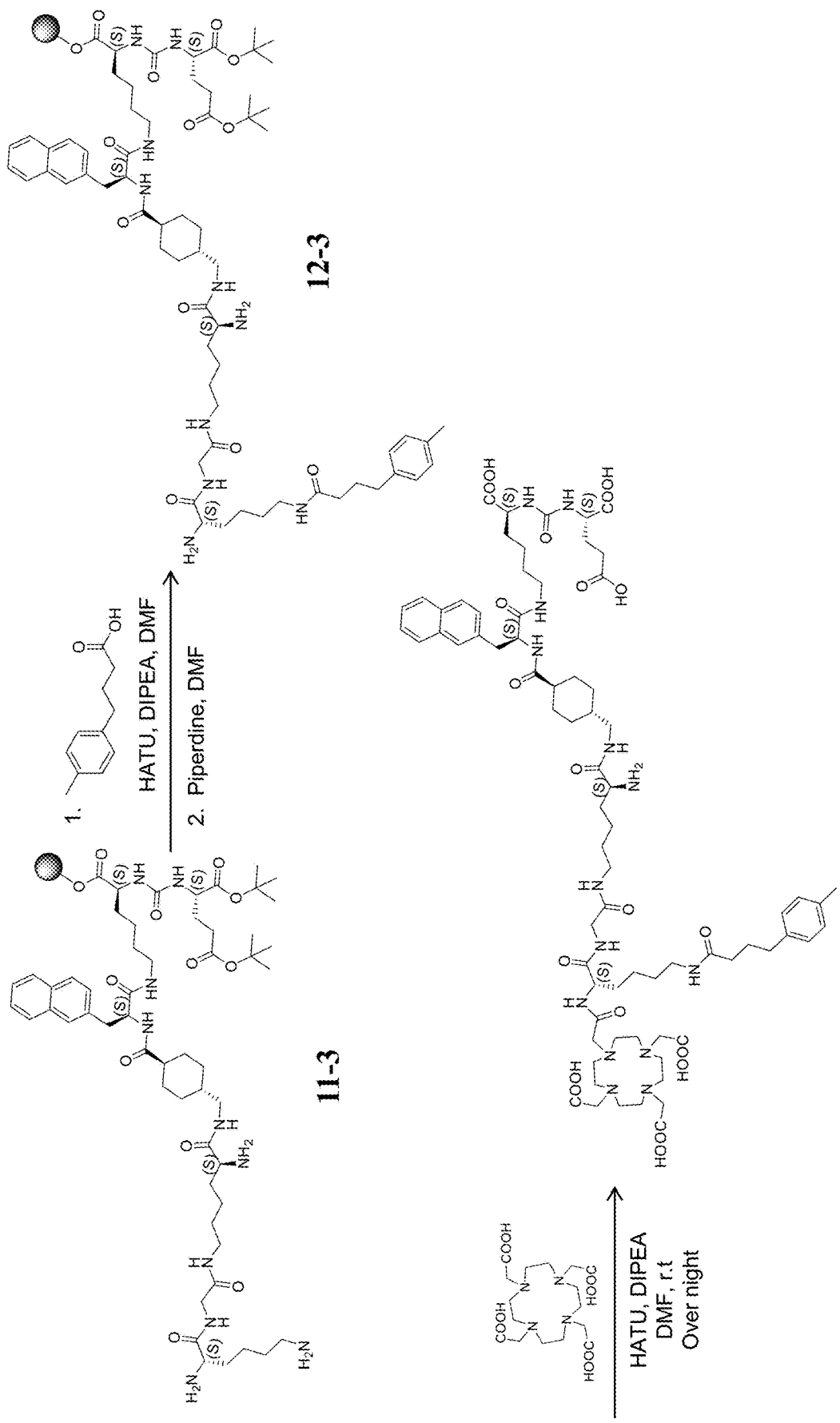

Fmoc-Lys-OH, HATU, DIPEA and Intermediate 8 were stirred at room temperature for 6 hours in DMF, and then piperidine was added for 4 hours to obtain compound 9-3. Fmoc-Gly-OH, HATU, DIPEA and compound 9-3 were stirred at room temperature for 6 hours and then piperidine was added for 4 hours to obtain compound 10-3. Fmoc-Lys-OH, HATU, DIPEA and compound 10-3 were stirred at room temperature for 6 hours and then piperidine was added for 4 hours to obtain compound 11-3. The benzene ring derivative, HATU, DIPEA and the compound 11-3 were stirred at room temperature for 6 hours, and then piperidine was added for 4 hours to obtain a compound 12-3. After DOTA, HATU, and DIPEA were pre-stirred in DMF for 15 minutes, the compound 12-3 was added to the reaction at room temperature overnight, and then stirred at room temperature for 2 hours in a solvent of trifluoroacetic acid to obtain MH-PC-AB-52 (FIG. 11A, 11B).

Figure 12A:
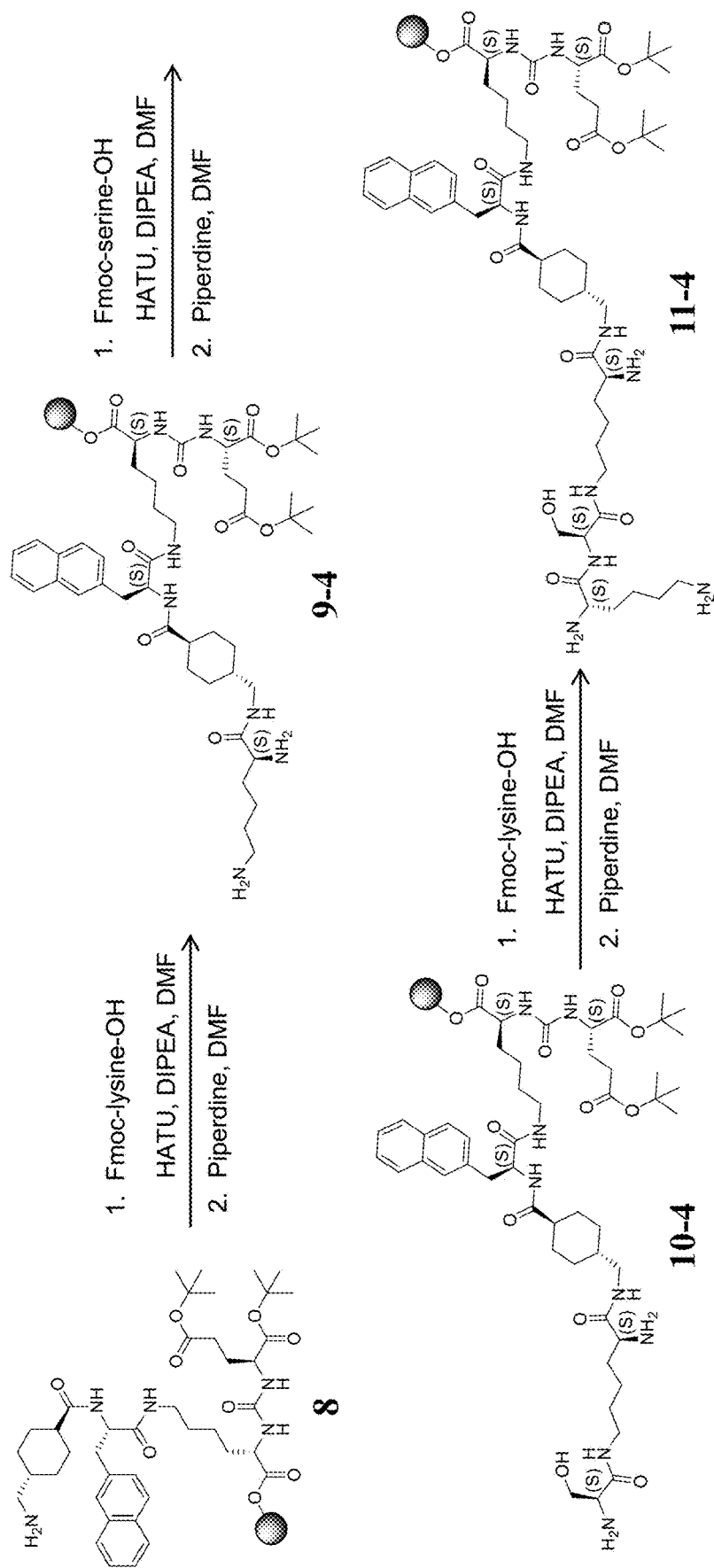
FIG. 12A, 12B shows PSMA inhibitor MH-PC-AB-X chemical synthesis process (5)
Figure 12B:
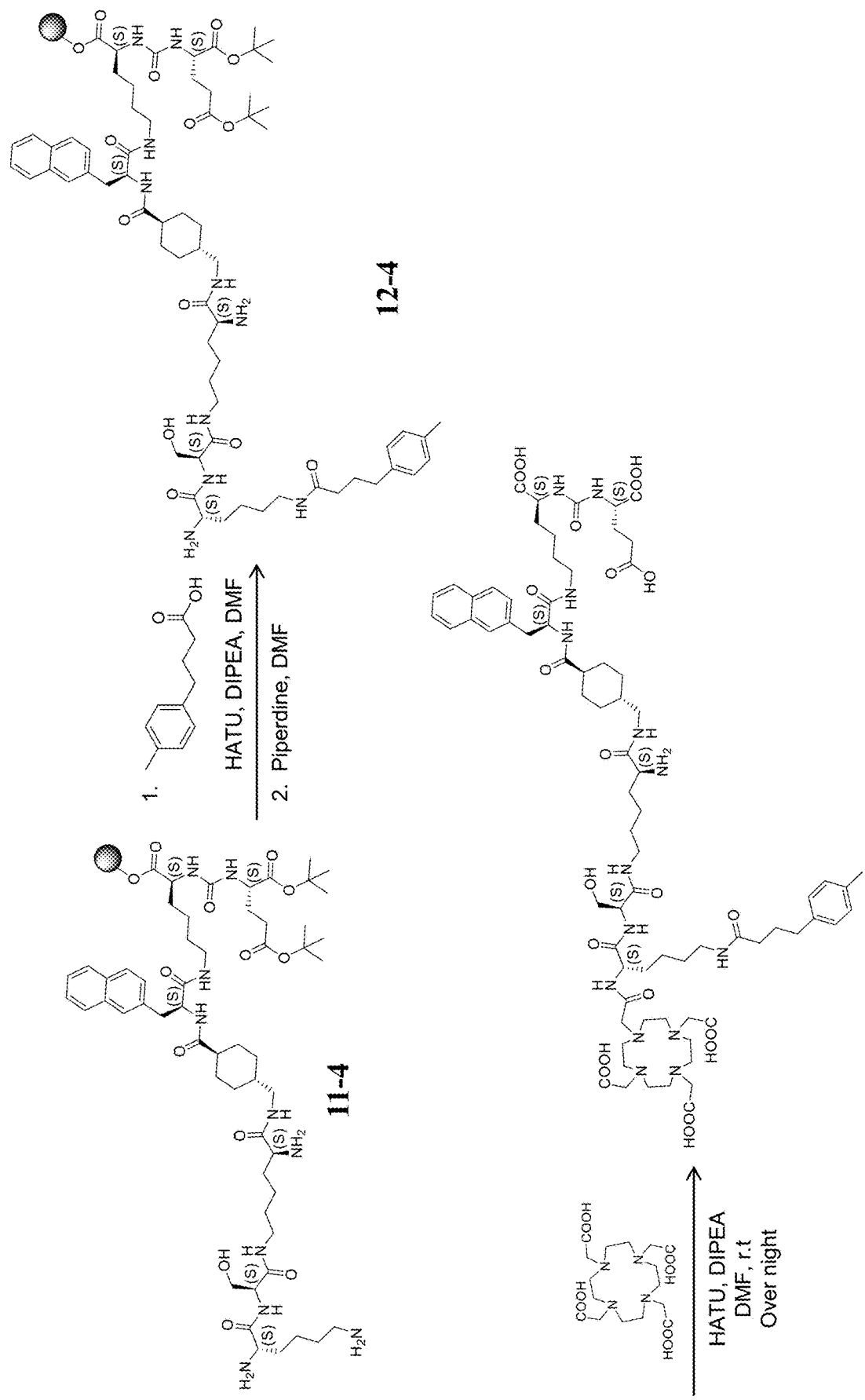

Fmoc-Lys-OH, HATU, DIPEA and Intermediate 8 were stirred at room temperature for 6 hours in DMF, and then piperidine was added for 4 hours to obtain compound 9-4. Fmoc-Ser-OH, HATU, DIPEA and compound 9-4 were stirred at room temperature for 6 hours and then piperidine was added for 4 hours to obtain compound 10-4. Fmoc-Lys-OH, HATU, DIPEA and compound 10-4 were stirred at room temperature for 6 hours and then piperidine was added for 4 hours to obtain compound 11-4. The benzene ring derivative, HATU, DIPEA and the compound 11-4 were stirred at room temperature for 6 hours, and then Piperidine was added for 4 hours to obtain a compound 12-4. After pre-stirring the DOTA, HATU, and DIPEA in DMF for 15 minutes, the compound 12-4 was added to the reaction at room temperature overnight, and then stirred at room temperature for 2 hours in a solvent of trifluoroacetic acid to obtain MH-PC-AB-53 (FIG. 12A, 12B).

Figure 13A:
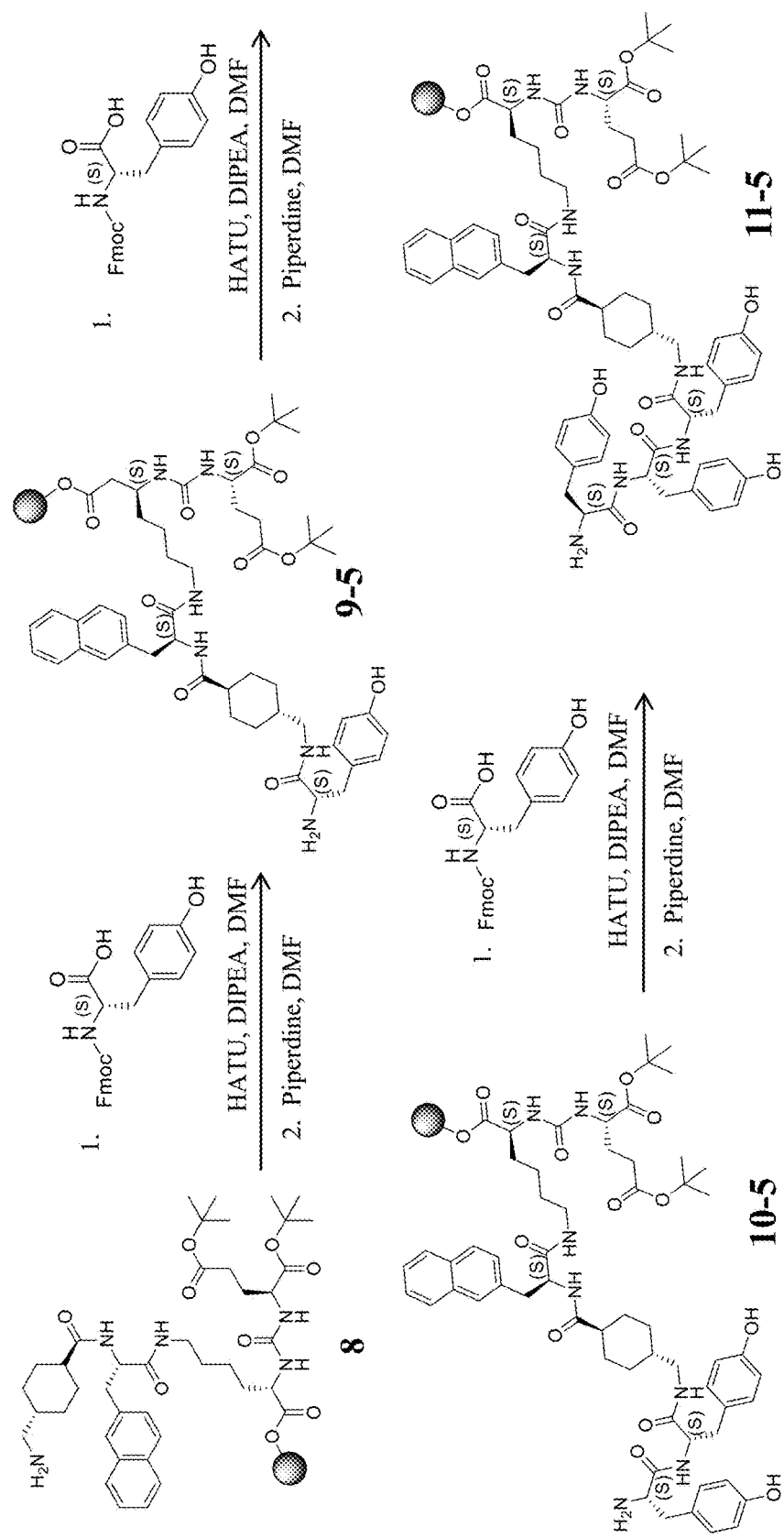
FIG. 13A, 13B shows PSMA inhibitor MH-PC-AB-X chemical synthesis process (6)
Figure 13B:
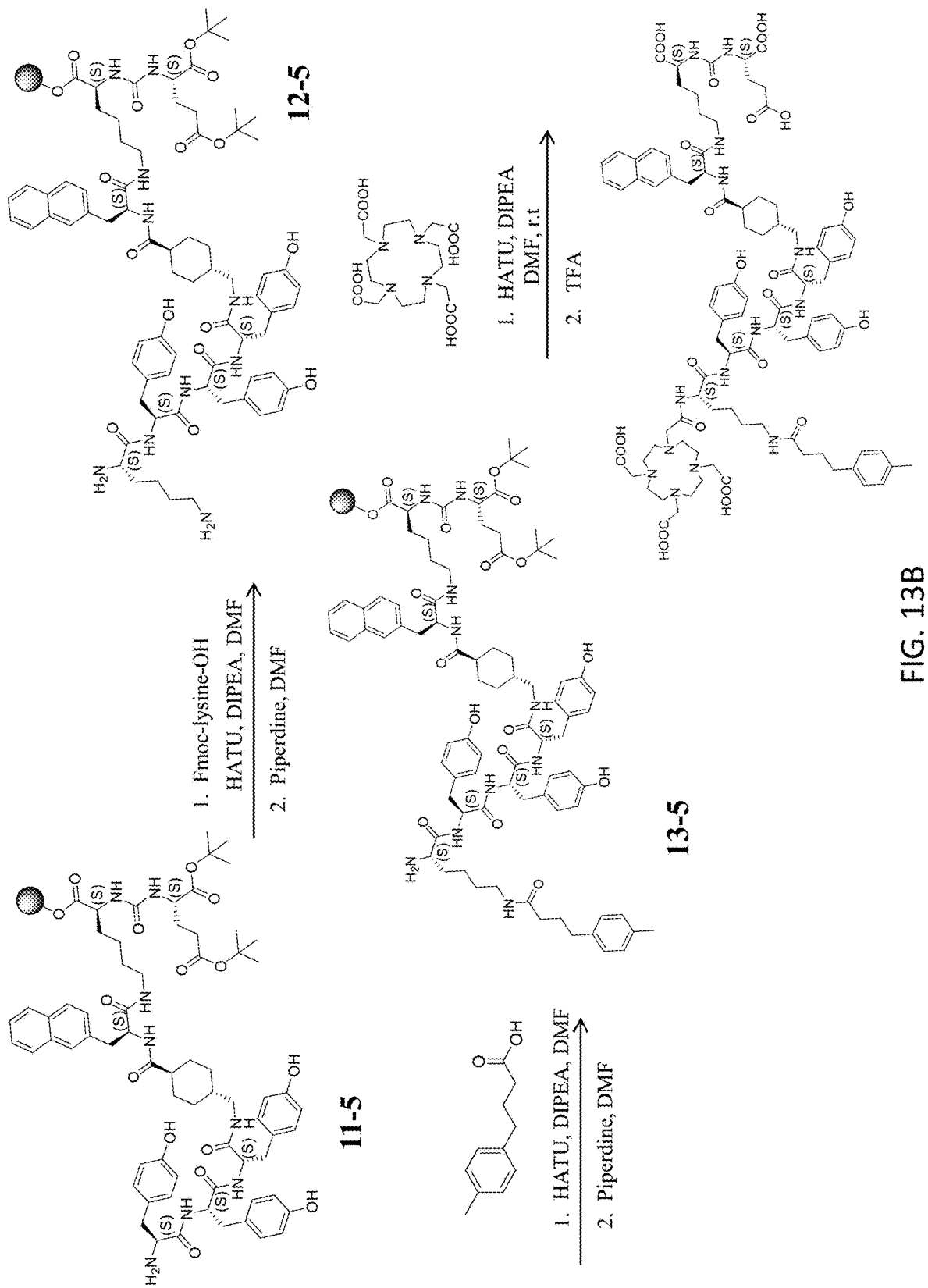

Fmoc-Ser-OH, HATU, DIPEA and Intermediate 8 were stirred at room temperature for 6 hours in DMF, and then piperidine was added for 4 hours to obtain compound 9-5. Fmoc-Ser-OH, HATU, DIPEA and compound 9-5 were stirred at room temperature for 6 hours and then piperidine was added for 4 hours to obtain compound 10-5. Fmoc-Ser-OH, HATU, DIPEA and compound 10-5 were stirred at room temperature for 6 hours, and then piperidine was added for 4 hours to obtain compound 11-5. Fmoc-Lys-OH, HATU, DIPEA and compound 11-5 were stirred at room temperature for 6 hours and then piperidine was added for 4 hours to obtain compound 12-5. The benzene ring derivative, HATU, DIPEA and compound 12-5 were stirred at room temperature for 6 hours and then piperidine was added for 4 hours to obtain compound 13-5. After DOTA, HATU, and DIPEA were pre-stirred in DMF for 15 minutes, the compound 13-5 was added to react at room temperature overnight, and then stirred at room temperature for 2 hours in a solvent of trifluoroacetic acid to obtain MH-PC-AB-57 (FIG. 13A, 13B).

Embodiment 2—The Method for Radiolabeled MH-PC-AB-X Preparation

Figure 14:
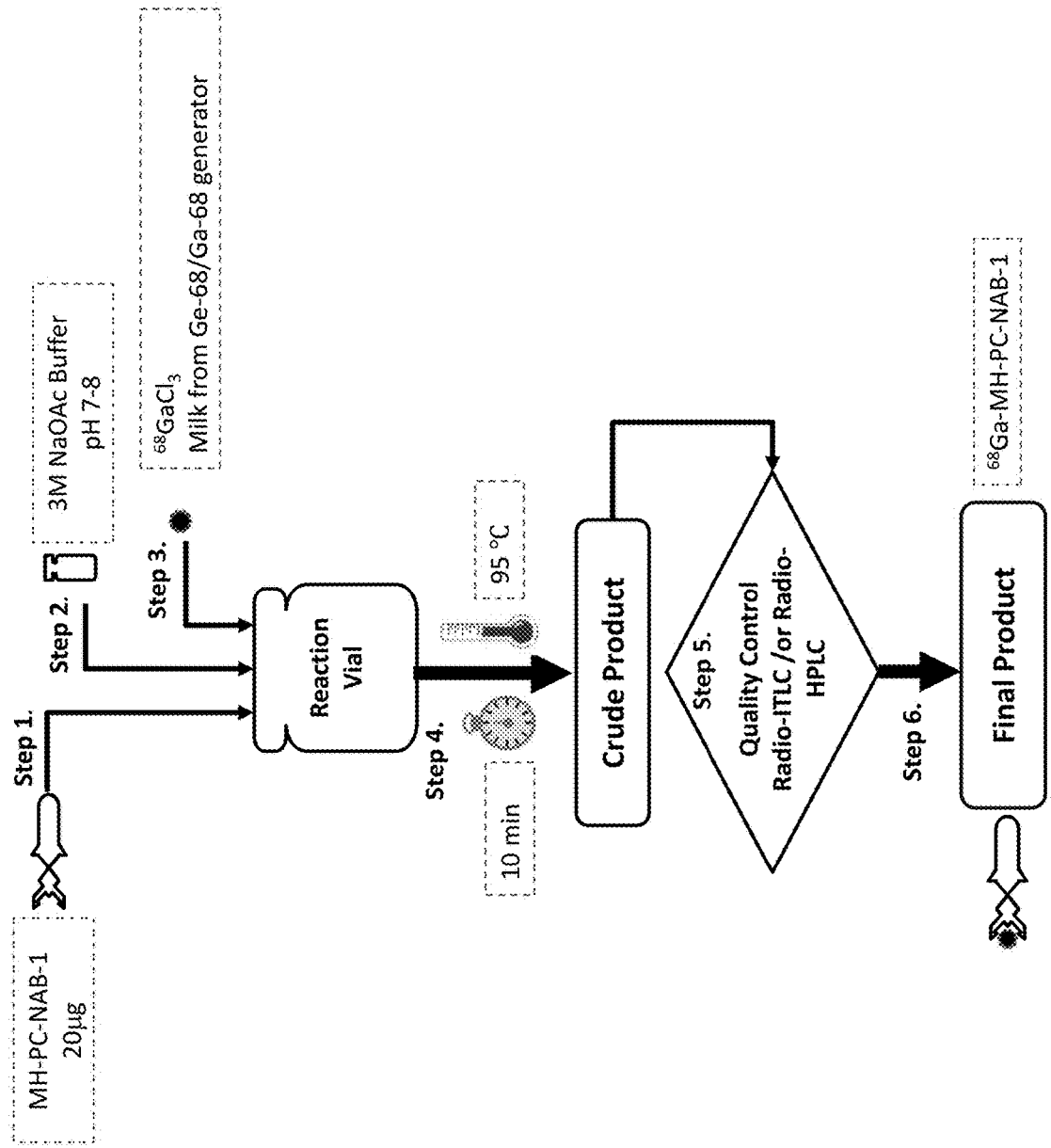
FIG. 14 shows flow chart of labeling Ga-68-MH-PC-NAB-1

MH-PC-AB-X was prepared in DMSO at 20 mg/mL, and placed in a microcentrifuge tube at 20 μg and stored at −20° C. The Ga-68 radionuclide labeling method (FIG. 14) was performed by taking 20 μg of MH-PC-NAB-1 into a 1.5 mL microcentrifuge tube and adding 3 M sodium acetate pH 7-8 buffer solution (NaOAc). Let the pH value of the final reaction solution be 3.7 or 4.7, respectively. After ultrasonic vibration for 1 to 2 min., add the Ga-68 source milked from the Ge-68/Ga-68 generator with initial activity about 1.6-3.0 mCi to be fully mixed and placed in a precision thermostat for heating at 95° C. for 10 minutes with vibration speed 500 rpm (FIG. 15).

Figure 16:
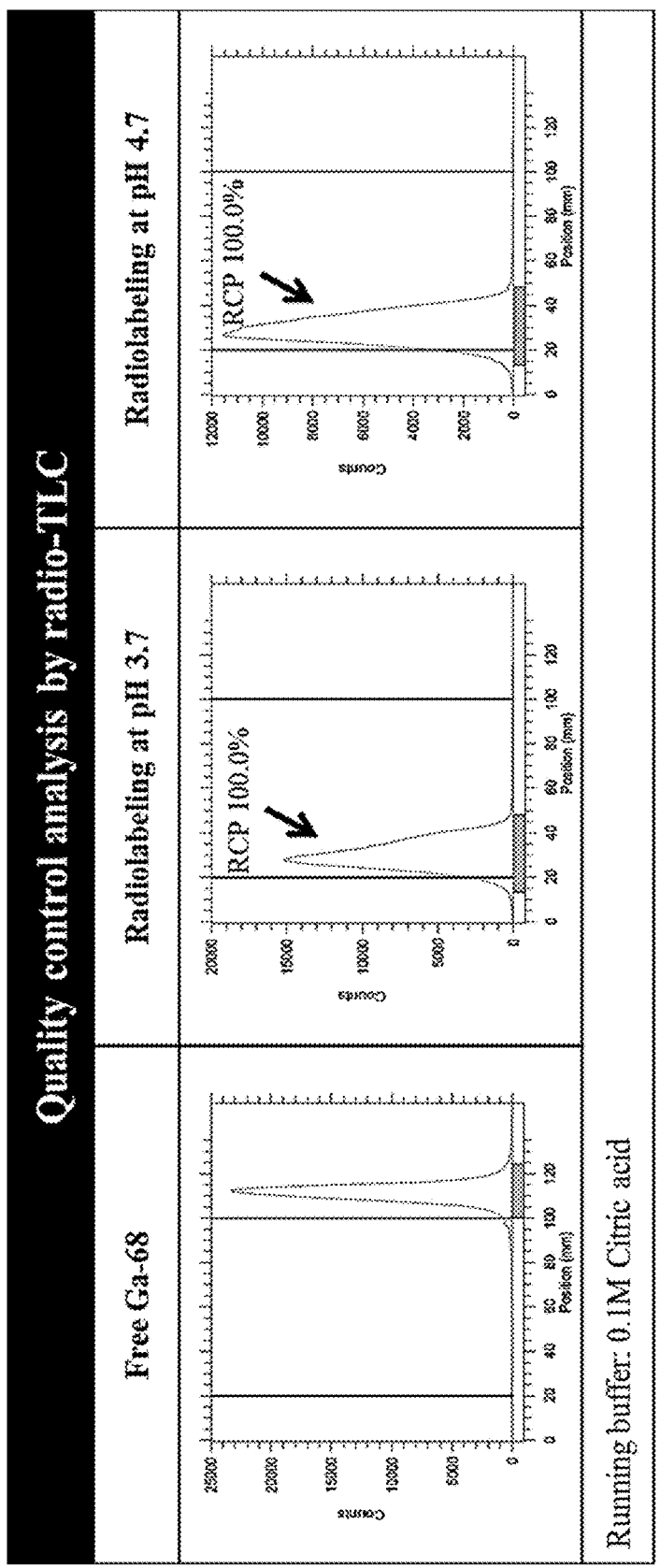
FIG. 16 shows Radio-ITLC analysis results of Ga-68-MH-PC-NAB-1
Figure 17:
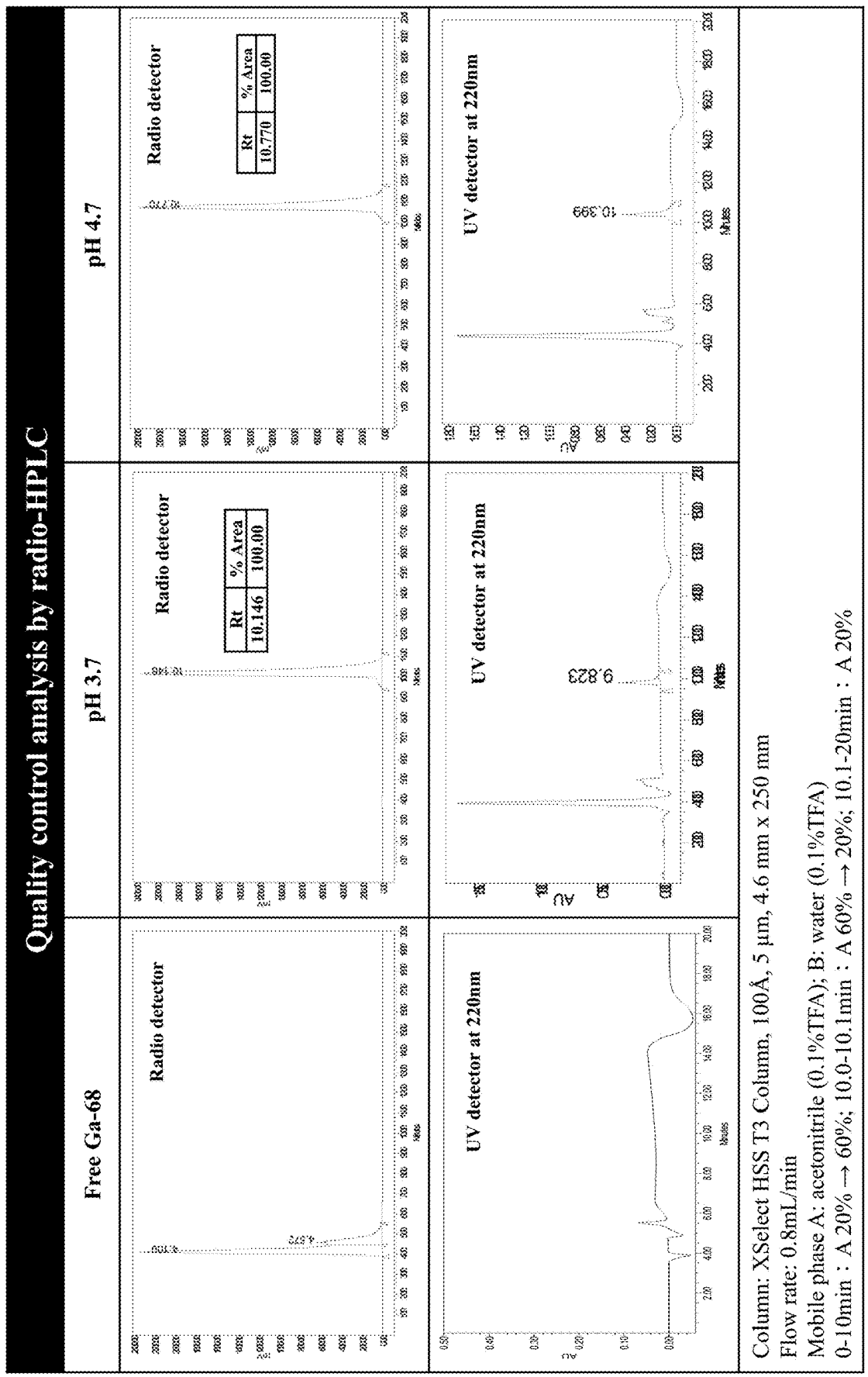
FIG. 17 shows Radio-HPLC analysis results of Ga-68-MH-PC-NAB-1

After complete cooling, take an appropriate amount of sample for Instant Thin Layer Chromatography (radio-ITLC) or radio High Pressure Liquid Chromatography (radio-HPLC). The Radio-ITLC is developed with 0.1M citric acid. The origin site is Ga-68-MH-PC-AB-X, and the solvent front is unreacted Ga-68. In radio-HPLC, the mobile phases are eluted with phase A and phase B. phase A is acetonitrile with 0.1% TFA and the phase B is deionized water with 0.1% TFA. The stationary phase is XSelect HSS T3 column (5 μm, 4.6 mm×250 mm). The mobile phase flow rate is 0.8 mL/min and run 20 minutes. The gradient profile: 0-10 minutes A is 20% to 60%, 10-10.1 minutes A is 60% to 20%, and 10.1-20 minutes A is 20%. The radiochemical purity is no less than 95% after 10 minutes of incubation time in buffer with each pH value presented above (FIGS. 16, 17).

Figure 18:
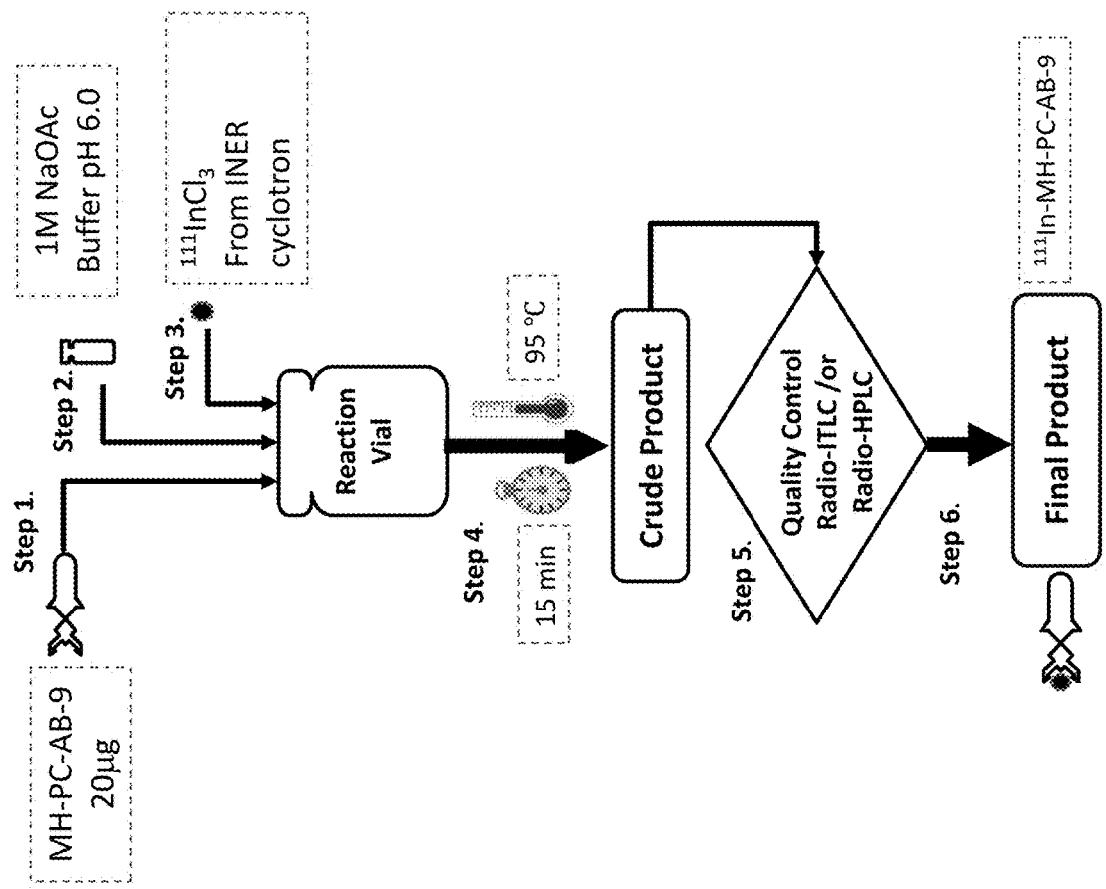
FIG. 18 shows flow chart of labeling In-111-MH-PC-AB-9
Figure 21:
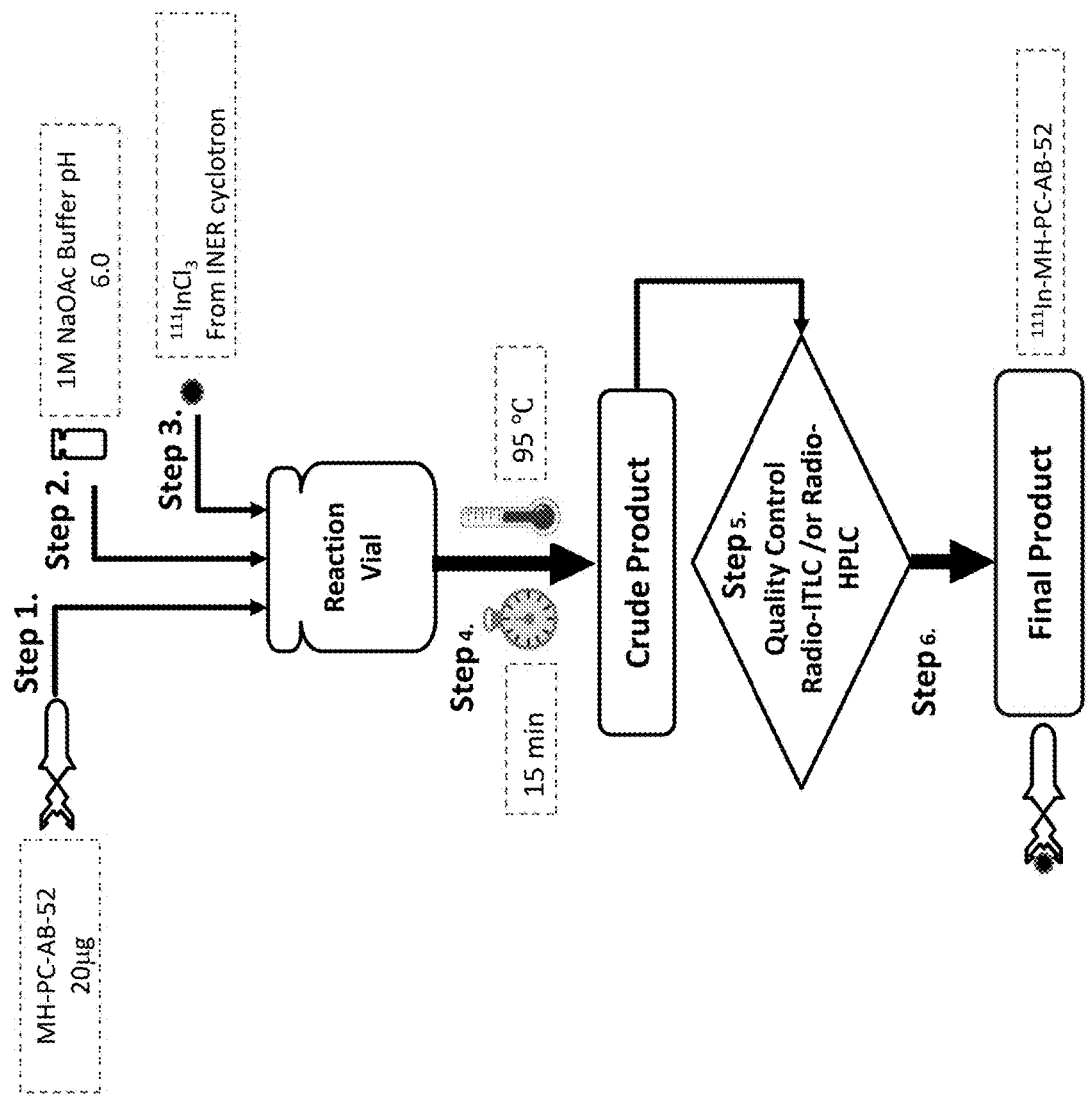
FIG. 21 shows flow chart of labeling In-111-MH-PC-AB-52
Figure 24:
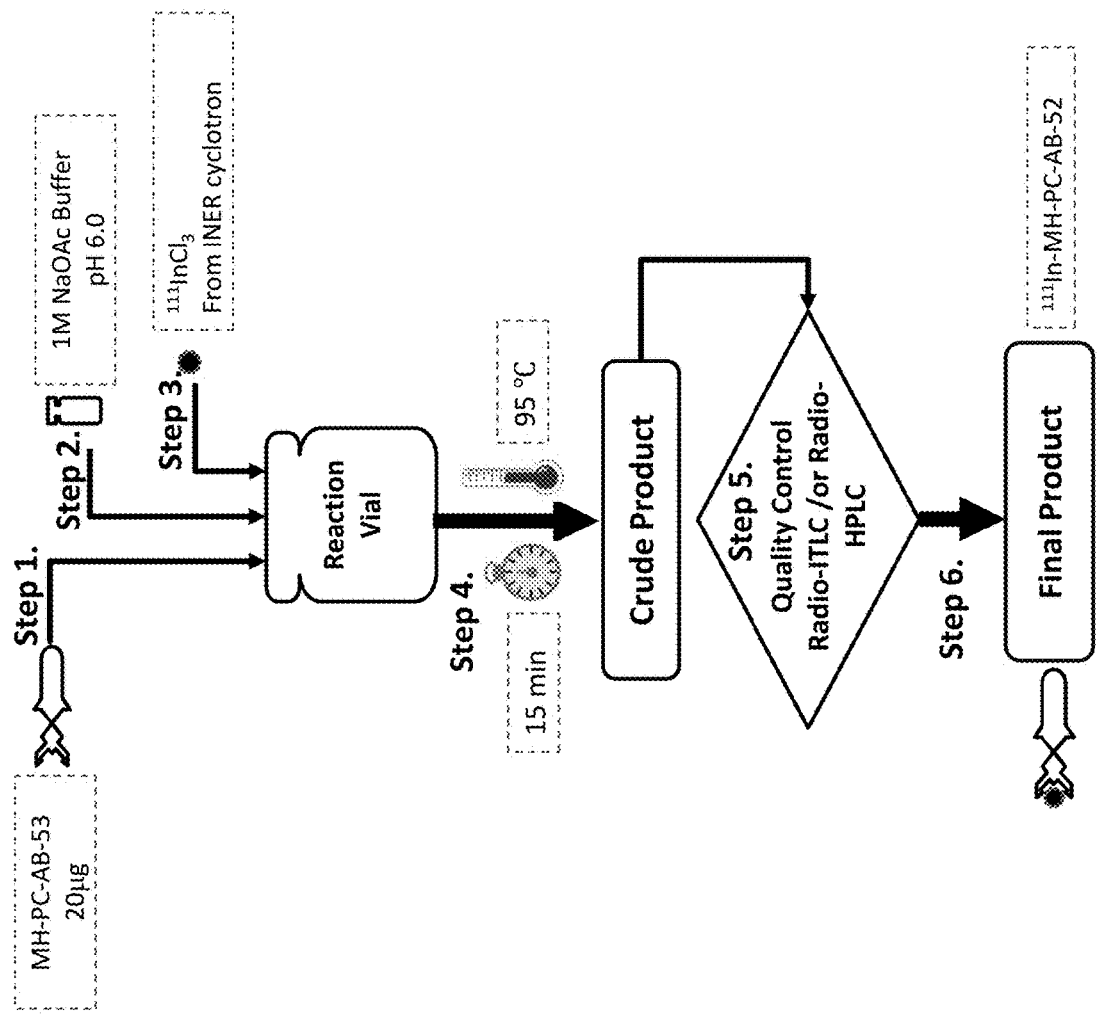
FIG. 24 shows flow chart of labeling In-111-MH-PC-AB-53

MH-PC-AB-X was prepared in DMSO at 20 mg/mL, and placed in a microcentrifuge tube at 20 μg, and stored at −20° C. The In-111 radionuclide labeling method was performed by taking 20 μg of MH-PC-AB-9 (FIG. 18), MH-PC-AB-52 (FIG. 21) and MH-PC-AB-53 (FIG. 24) into 1.5 mL microcentrifuge tube, add 1.0 M sodium acetate pH6 buffer solution (NaOAc), sonicate for 1 to 2 min with ultrasonic wave, and then add In-111 source produced from INER cyclotron with initial activity of about 3.0 mCi, after mixed evenly, it was placed in a precision thermostat controller for heating at 95° C. for 15 minutes, and the vibration speed is 500 rpm (FIG. 19, 22, 25).

Figure 20:
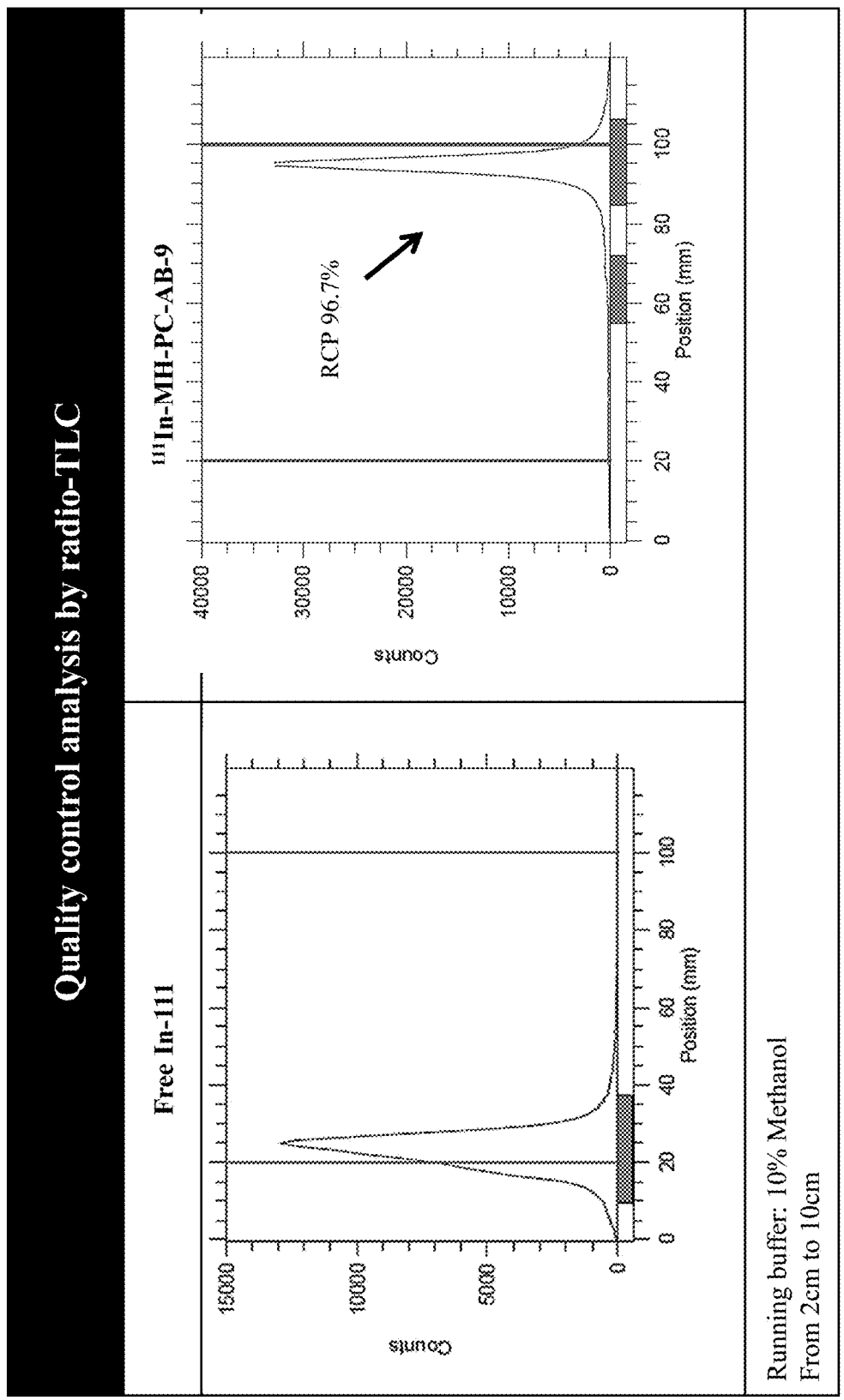
FIG. 20 shows Radio-ITLC analysis results of In-111-MH-PC-AB-9
Figure 23:
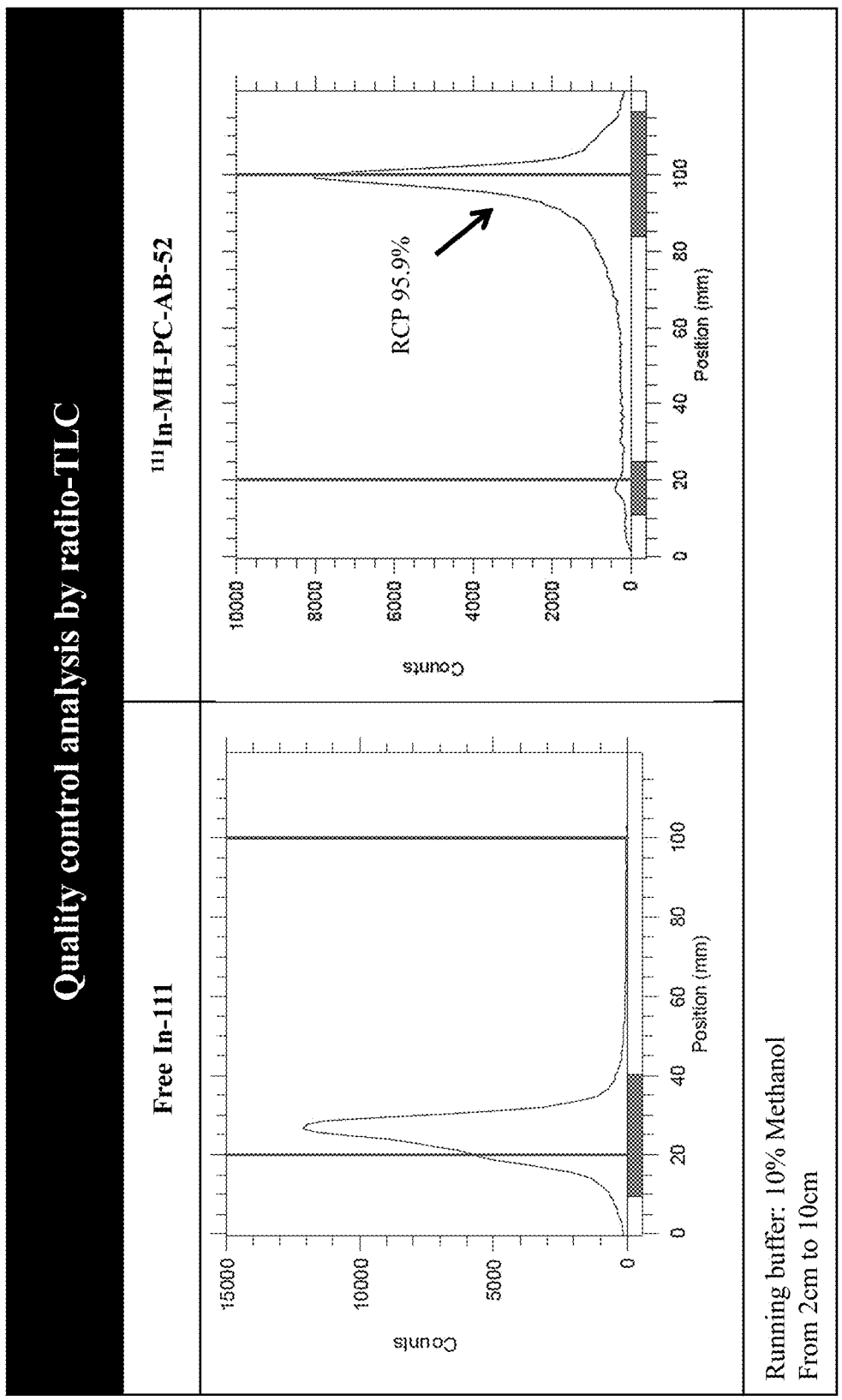
FIG. 23 shows Radio-ITLC analysis results of In-111-MH-PC-AB-52
Figure 26:
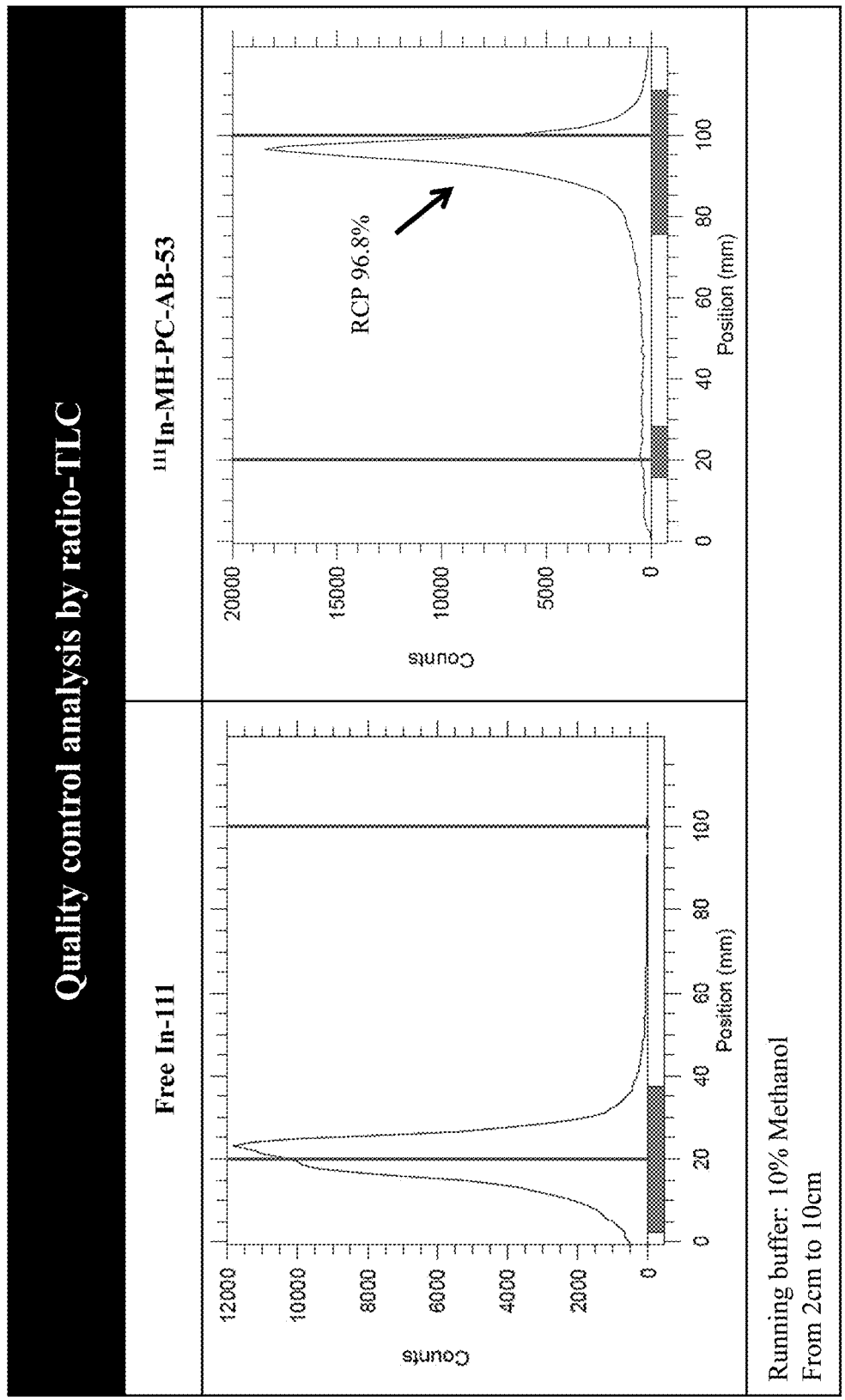
FIG. 26 shows Radio-ITLC analysis results of In-111-MH-PC-AB-53

After complete cooling, an appropriate amount of sample is taken for radioactive instant thin layer analysis (radio-ITLC). With radiation instant thin layer analysis method, the analysis development solution is 10% methanol, the origin site In-111-MH-PC-AB-X, and the solvent front is unreacted In-111, the radiochemical purity can be no less than 95% after 15 minutes of incubation time (FIGS. 20, 23, 26).

Figure 27:
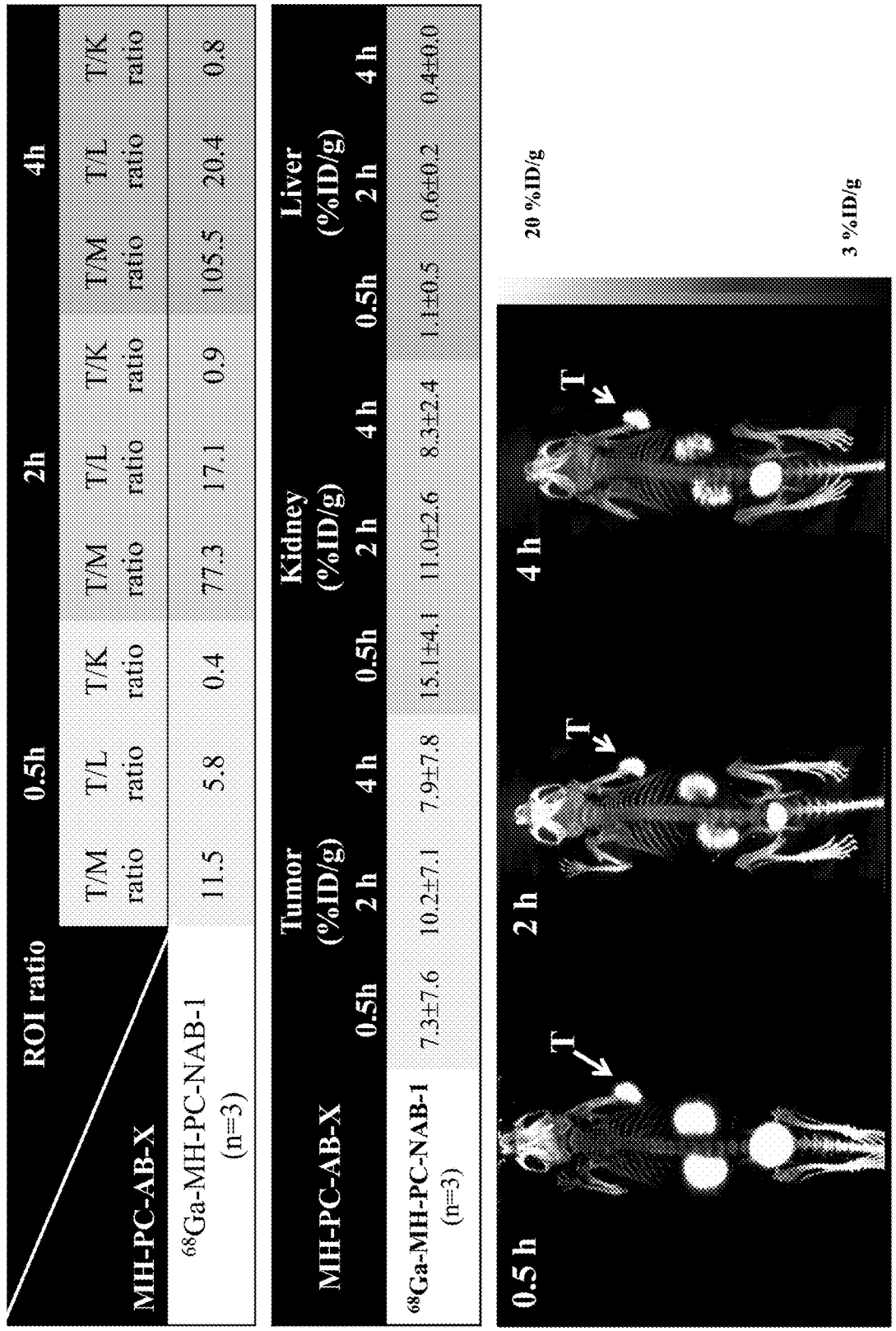
FIG. 27 shows Ga-68-MH-PC-NAB-1 in LNCaP human prostate cancer tumor animal model NanoPET/CT contrast
Figure 30:
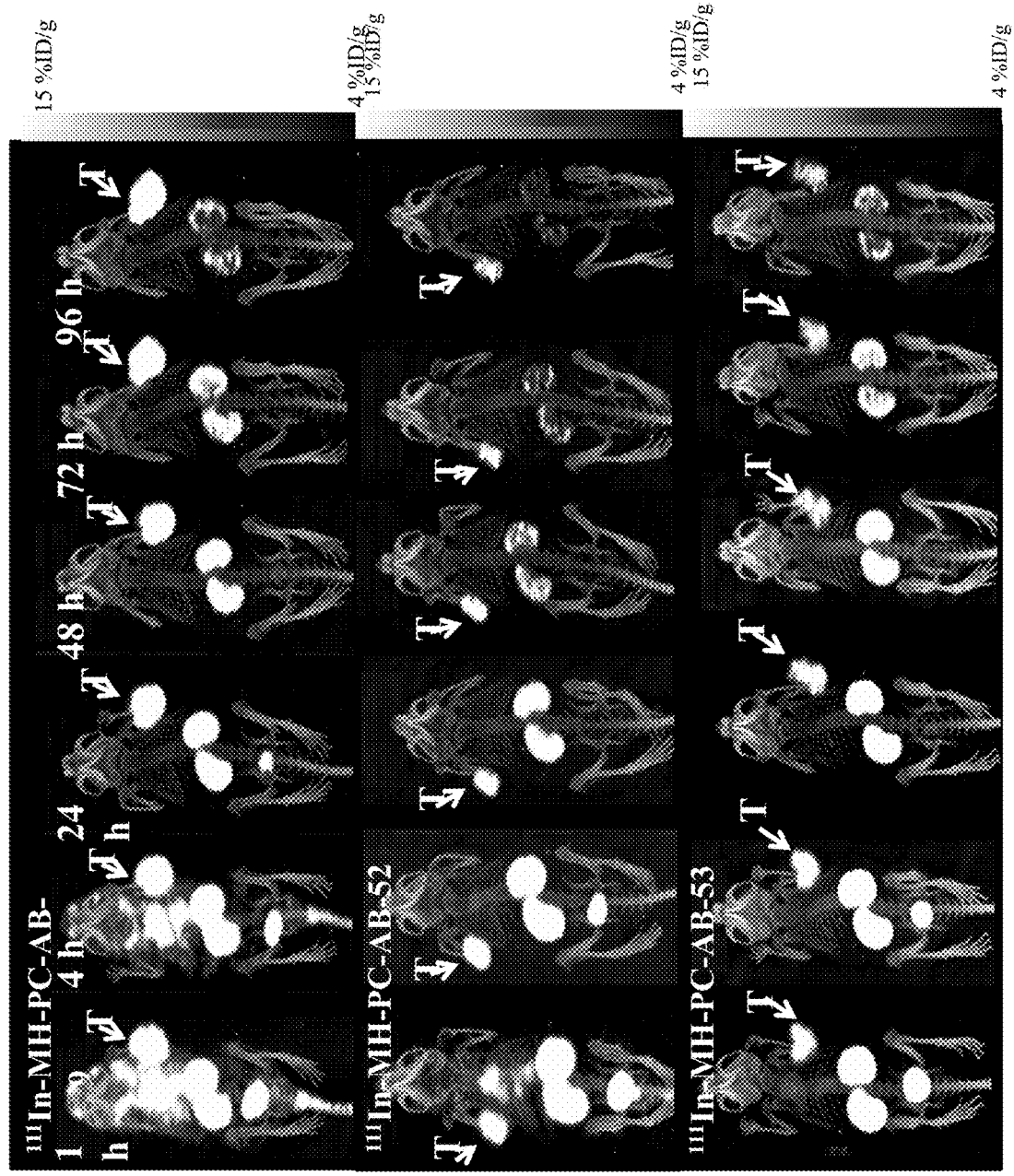
FIG. 30 shows In-111-MH-PC-AB-X in LNCaP human prostate cancer tumor animal model NanoSPECT/CT angiogram

Embodiment 3—Application of Radiolabeled MH-PC-AB-X for Human Prostate Cancer Tumor Model PSMA expressed NCaP human prostate cancer cells were inoculated at 4×10$^6$ to the right forelimb of SCID mice. After about 3 week of inoculation, MH-PC-AB was labeled with radioisotope Ga-68 or In-111, and Ga-68-MH-PC-AB-X or In-111-MH-PC-AB-X with radiochemical purity greater than 95% adjusted to a specific activity of 5 μCi/μL with water for injection, and the tumor bearing mice were injected with 500 μCi Ga-68-MH-PC-AB-X or In-111-MH-PC-AB-X by tail vein injection. The nanoPET/CT scans were performed at 0.5, 2 and 4 hours after injection of Ga-68-MH-PC-AB-X (FIG. 27). The nanoSPECT/CT scans were performed at 1, 4, 24, 48, 72 and 96 hours after injection of In-111-MH-PC-AB-X (FIG. 30).

Using nanoPET/CT or nanoSPECT/CT scans to follow up on the distribution of the radioactive drug in mice. The region of interest (ROI) of target organs was semi-quantified with known activity of reference standard. The linear proportional formula between the PET or SPECT count value and the actual activity is obtained from the reference radioactivity of each time point. And the interest region of scan image on analysis software is defined, and the radioactivity/volume of each target organ is obtained through interpolation or extrapolation of the linear formula.

Figure 28:
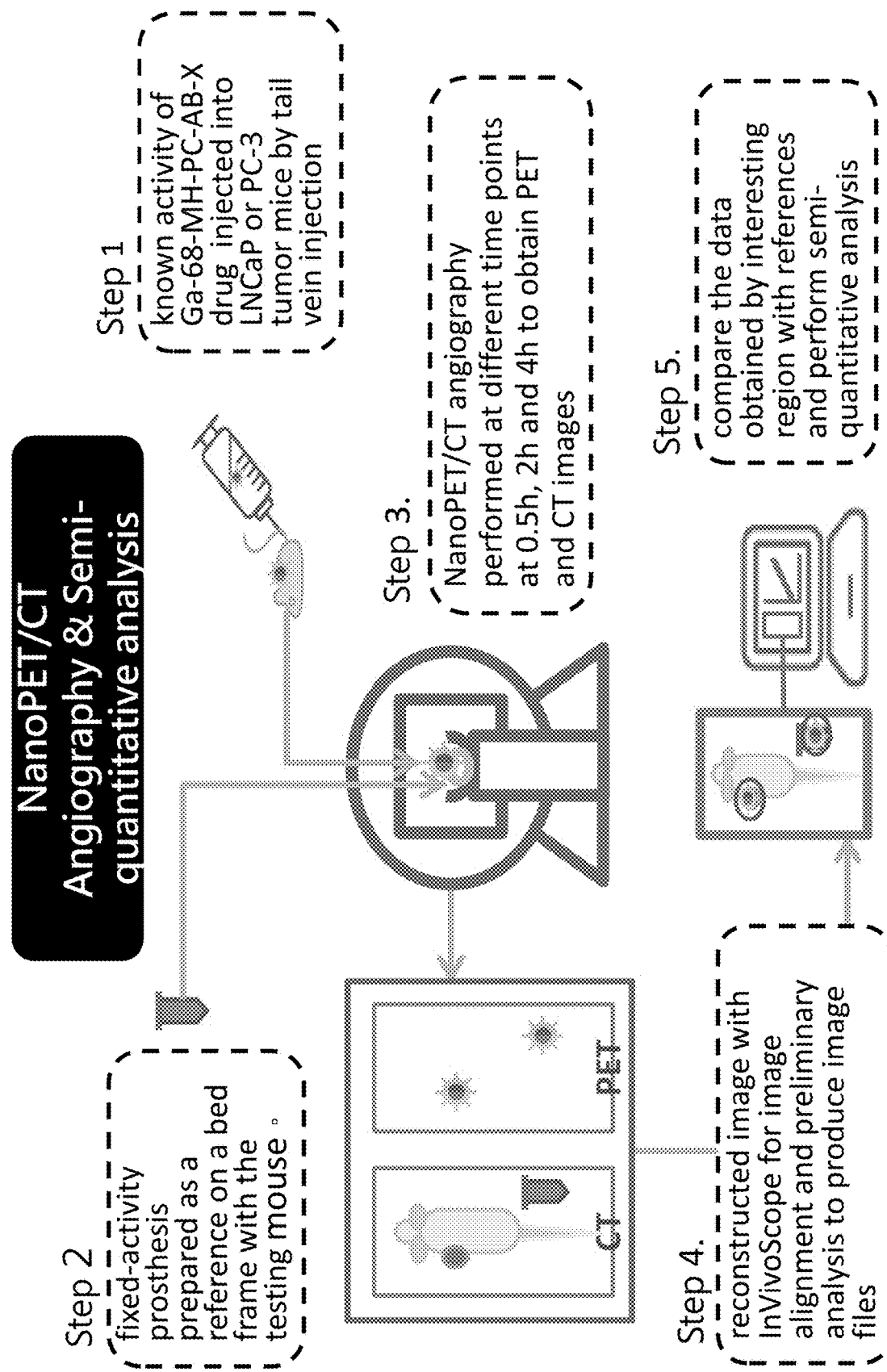
FIG. 28 shows NanoPET/CT angiography and image semi-quantitative flow chart
Figure 31:
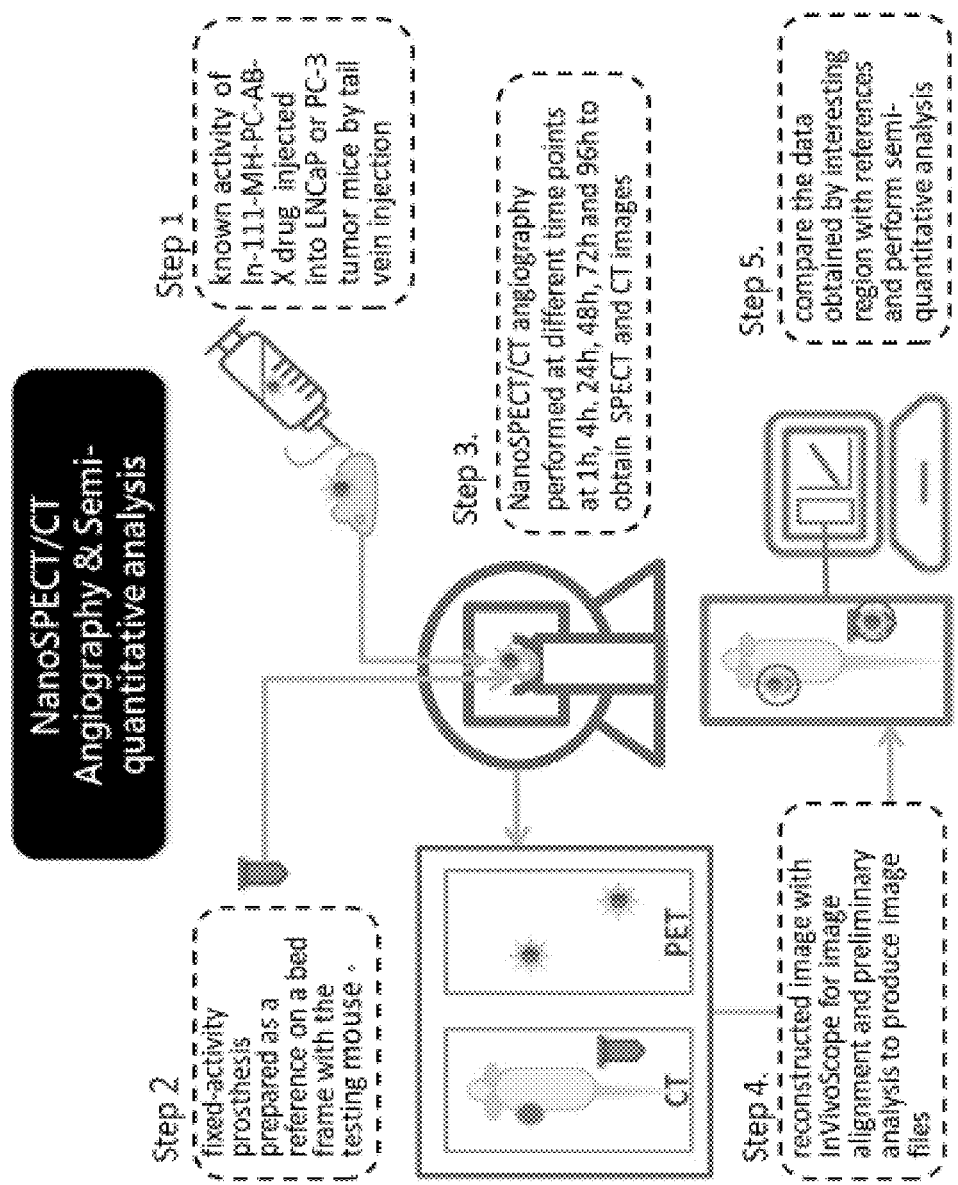
FIG. 31 shows NanoSPECT/CT angiography and semi-quantitative flow chart

The semi-quantification assumes 1 mL of injected compounds equal to 1 gram and 1cm³ of the interest region of scan image is equal to 1 gram. The radioactivity per injection volume and mice's weight are known, so we can obtain the ratio of the distribution of 1 gram Ga-68-MH-PC-AB-X or In-111-MH-PC-AB-X in each organ (% ID/g). The organ distribution ratio of interesting organs is calculated, including tumor (symbol T), liver (symbol L) and kidney (symbol K), as shown in FIG. 29 and FIG. 32. The process of semi-quantification of nanoPET/CT and nanoSPECT/CT are presented in FIG. 28 and FIG. 31, respectably.

What is claimed is:

1. A PSMA inhibitor of structure

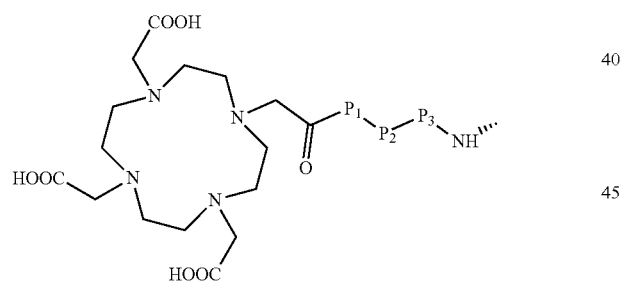

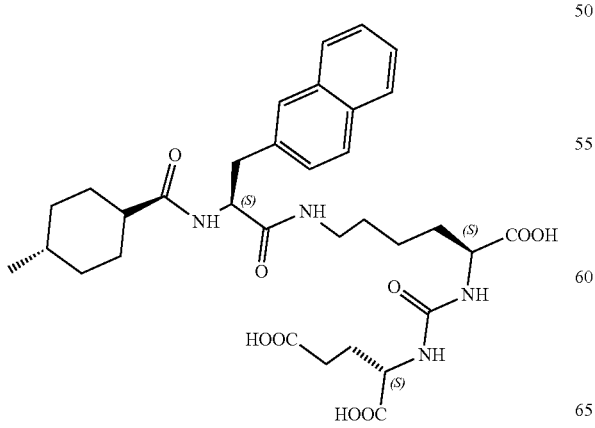

wherein P1 is selected from the group consisting of

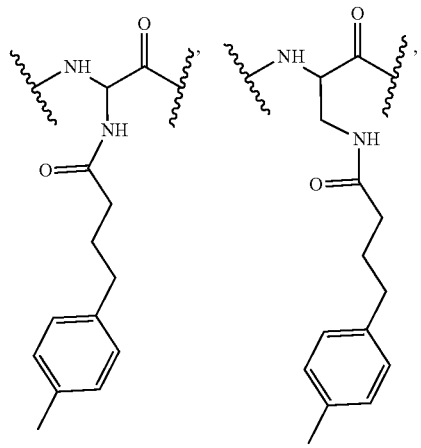

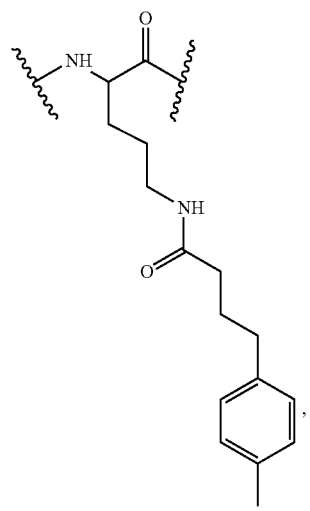

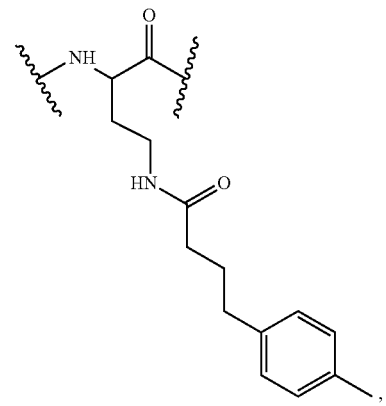

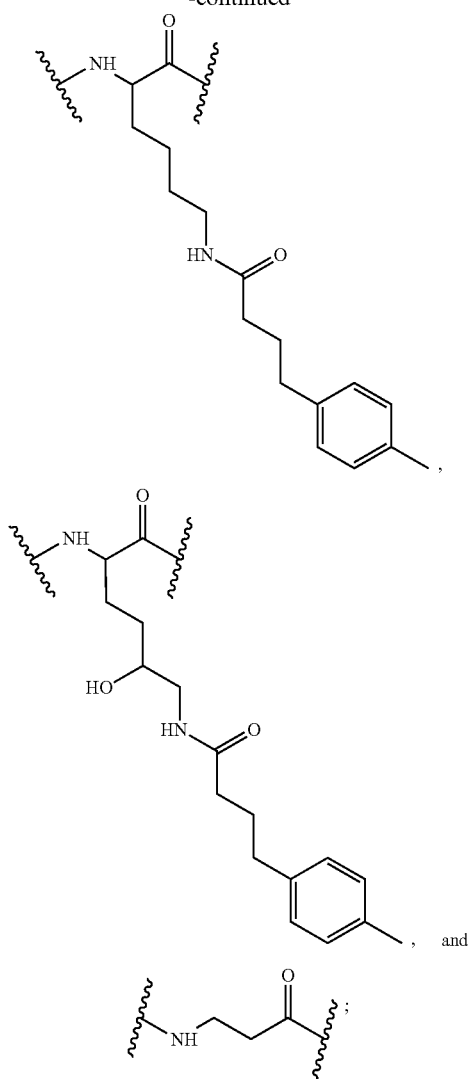
P2 is selected from the group consisting of
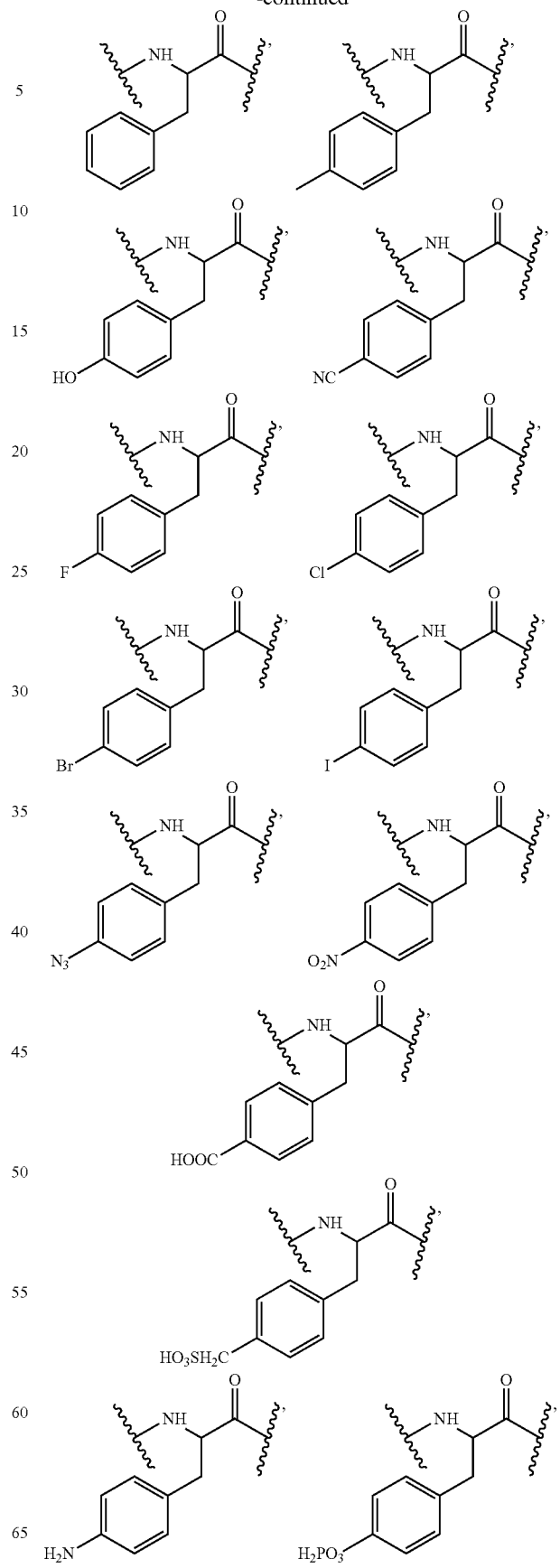

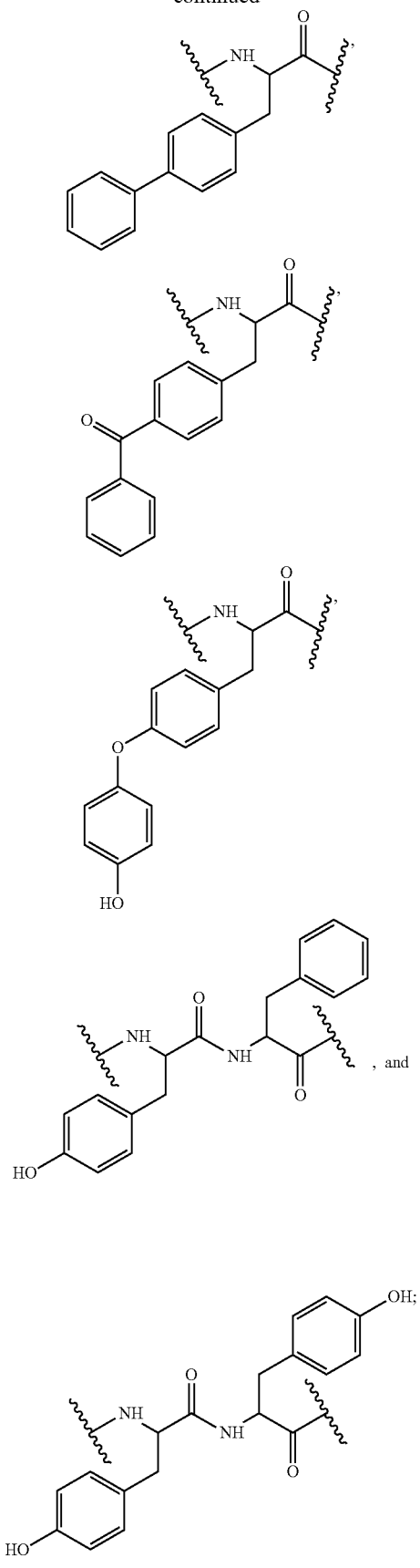
and P3 is selected from the group consisting of

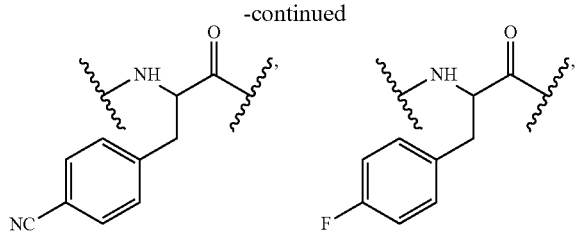
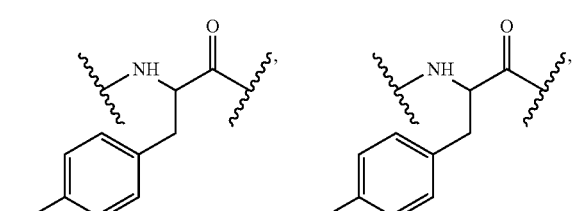
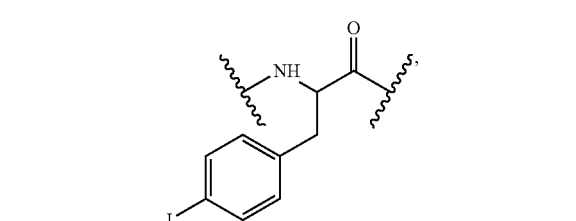
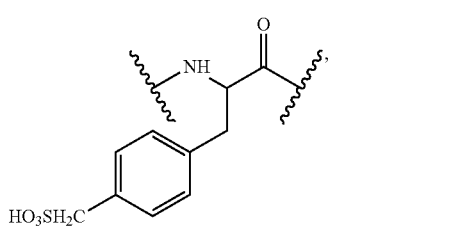
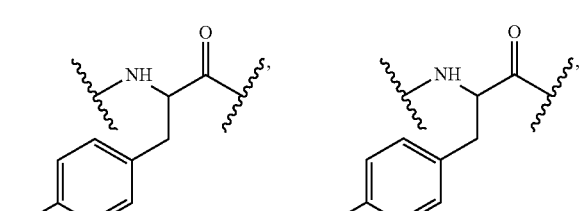
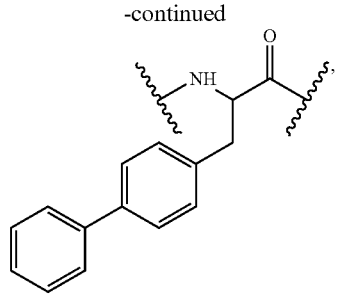
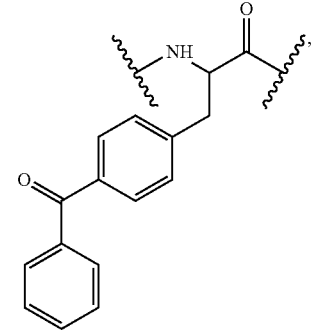
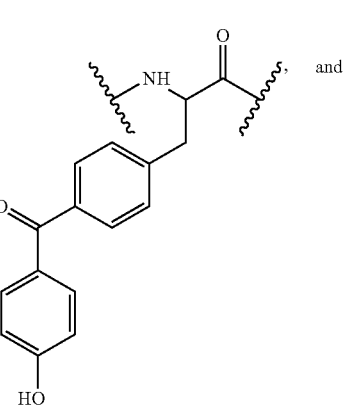
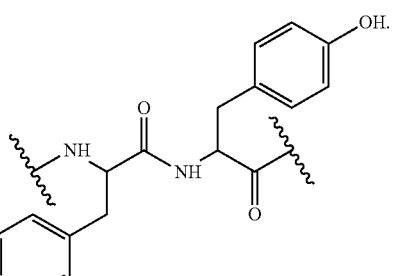
2. The PSMA inhibitor of claim 1 further comprising a radionuclide selected from the group consisting of Ga-68, Ga-67, In-111, Cu-64, Lu-177, and Y-90.

3. The PSMA inhibitor structure of claim 1 selected from the group consisting of
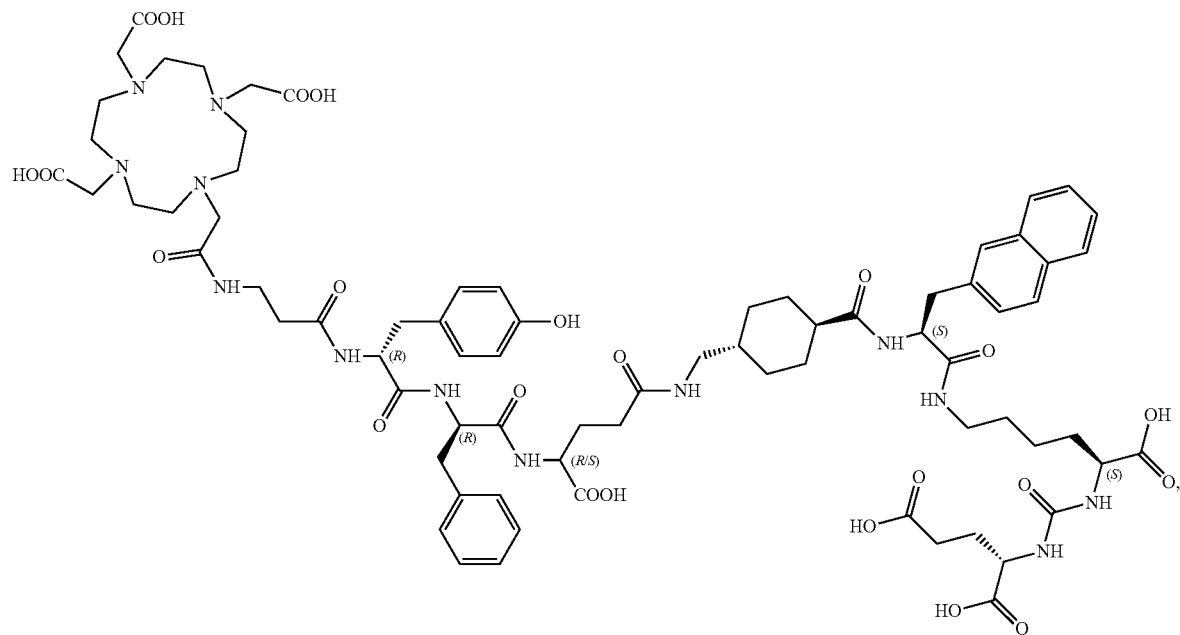
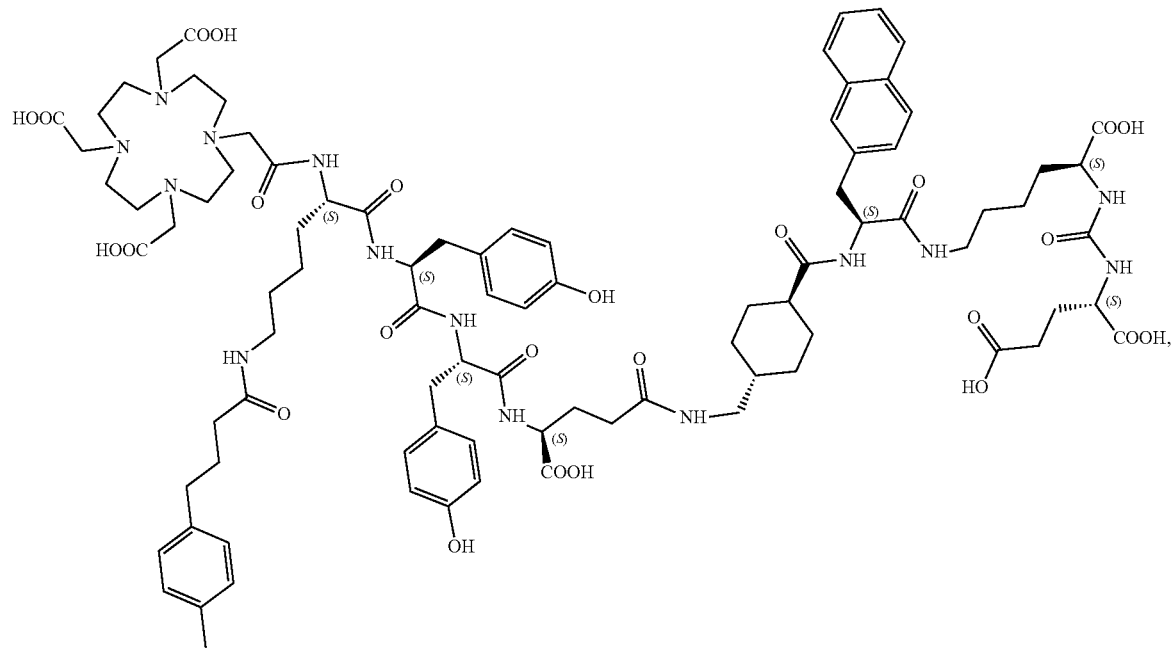

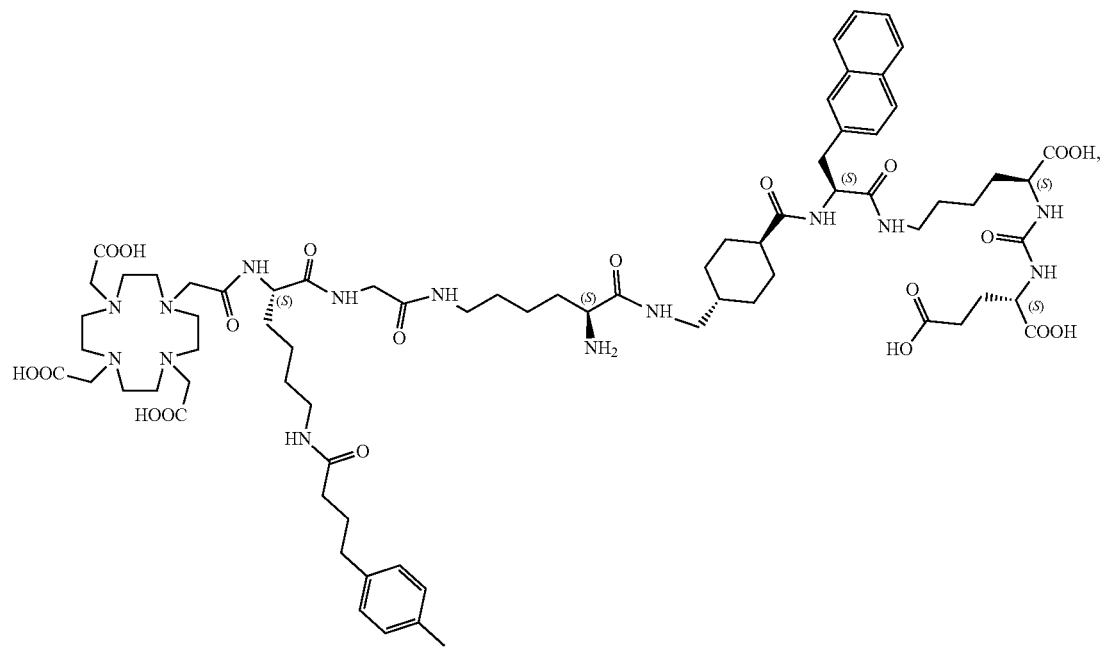
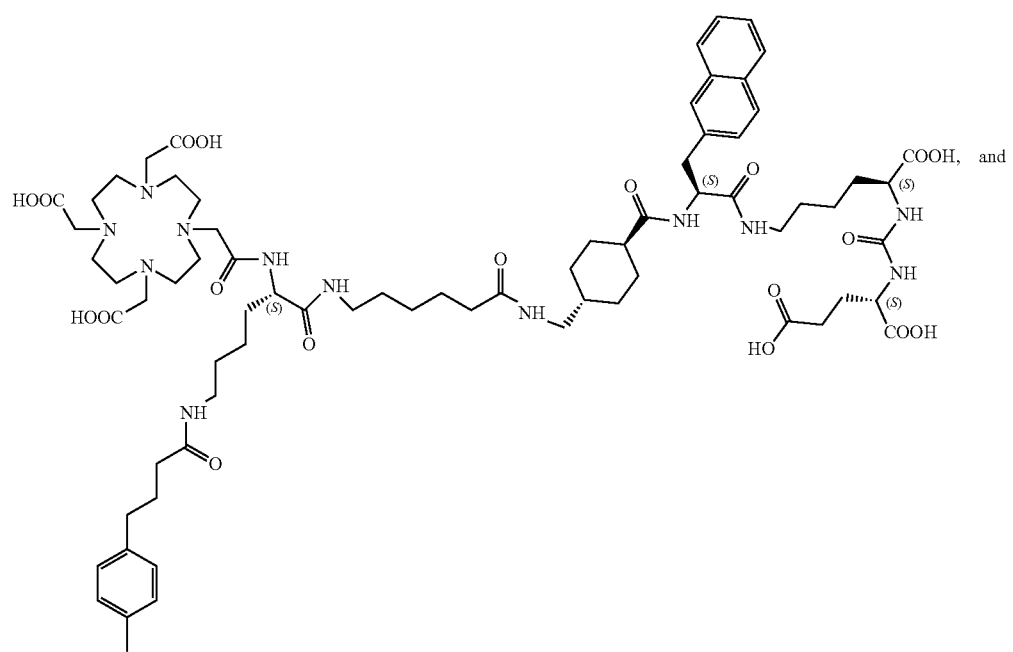

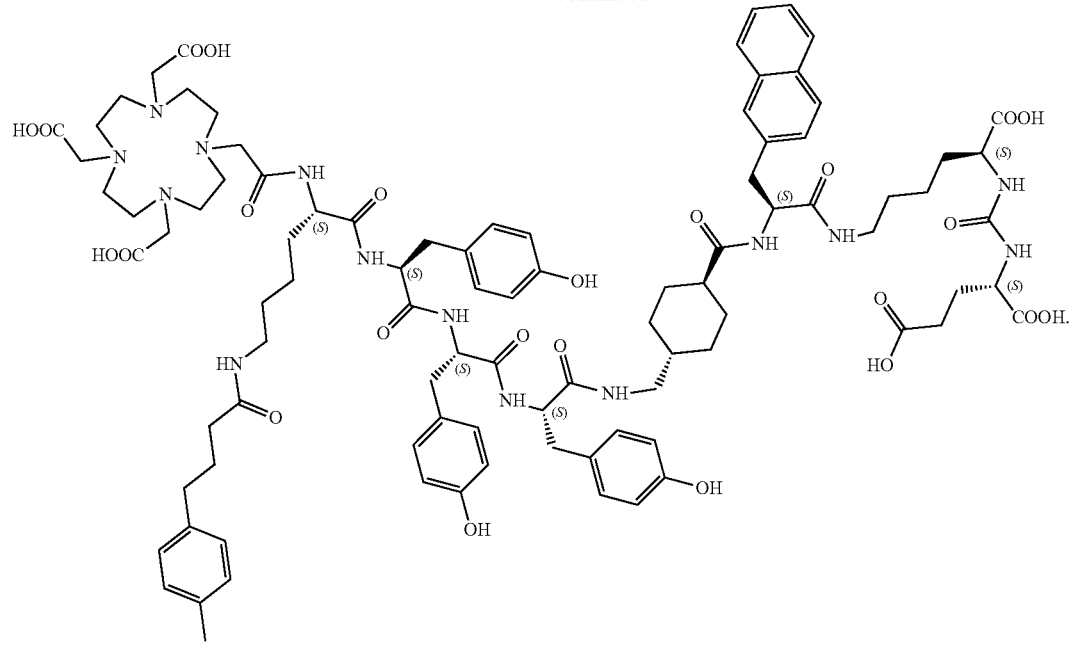
* * * * *